United States Patent [19]
Asai et al.

[11] Patent Number: 5,416,231
[45] Date of Patent: May 16, 1995

[54] PROSTAGLANDIN $I_2$ DERIVATIVES

[75] Inventors: Tomoyuki Asai; Yoshitomo Morizawa; Arata Yasuda, all of Yokohama; Taku Yamamoto, Toyonaka; Buichi Fujitani, Sakai; Kanoo Hosoki, Toyonaka, all of Japan

[73] Assignee: Asahi Glass Company, Ltd., Tokyo, Japan

[21] Appl. No.: 983,845

[22] PCT Filed: Sep. 5, 1991

[86] PCT No.: PCT/JP91/01185

§ 371 Date: Apr. 9, 1993

§ 102(e) Date: Apr. 9, 1993

[87] PCT Pub. No.: WO92/04339

PCT Pub. Date: Mar. 19, 1992

[30] Foreign Application Priority Data

Sep. 7, 1990 [JP] Japan .................. 2-235758

[51] Int. Cl.$^6$ .................................... C07D 307/935
[52] U.S. Cl. ............................................ 549/465
[58] Field of Search ............. 549/465; 562/118

[56] References Cited

U.S. PATENT DOCUMENTS 4,273,784 6/1981 Bollinger .

FOREIGN PATENT DOCUMENTS 2198131 6/1988 United Kingdom .

OTHER PUBLICATIONS

Journal of Pharmacology and Experimental Therapeutics, vol. 206, No. 1, Jul. 1978 (Baltimore, US) B. H. Crane et al.: "Effect of prostaglandin $I_2$ and analogs on platelet aggregation and smooth muscle contraction", pp. 132–138.

*Primary Examiner*—Robert Gerstl
*Attorney, Agent, or Firm*—Oblon, Spivak, McClelland, Maier & Neustadt

[57] ABSTRACT

A novel prostaglandin $I_2$ derivative selected from a prostaglandin $I_2$ having a halogen atom on the carbon atom corresponding to the 7-position of natural prostaglandin $I_2$ and having a cycloalkylene group in the α-chain, and its esters and salts.

13 Claims, No Drawings

PROSTAGLANDIN I₂ DERIVATIVES

TECHNICAL FIELD

The present invention relates to novel prostaglandin $I_2$ derivatives. More particularly, the present invention relates to prostaglandins $I_2$ having a halogen atom, particularly a fluorine atom, on the carbon atom corresponding to the 7-position of natural prostaglandin $I_2$ and having a cycloalkylene group in the α-chain, and their esters and salts, which will hereinafter be referred to generally as prostaglandin $I_2$ derivatives. Further, the present invention relates to pharmaceutical compositions containing such prostaglandin $I_2$ derivatives as active ingredients. In this specification, prostaglandin may sometimes be referred to simply as PG.

BACKGROUND ART

Natural $PGI_2$ is a local hormone product in vivo mainly at the endothelium of arterial vessels, and it is an important factor for controlling cell functions in vivo by its strong physiological activities such as an antiplatelet activity and a vasodilating activity. There has been an attempt to use it directly as a drug (P. J. Lewis, J. O. Grandy et al, Clinical Pharmacology of Prostacyclin Raven Press, N.Y., 1981). However, natural $PGI_2$ has in its molecule a vinyl ether bond which is susceptible to hydrolysis and is readily deactivated under a neutral or acidic condition. Thus, because of its chemical instability, it can not be regarded as a good compound for a drug. Therefore, studies have been made to develop chemically stable synthetic $PGI_2$ derivatives having physiological activities equal to natural $PGI_2$. Among them, there is a report on a case wherein a fluorine atom was introduced to various sites ("Journal of Synthetic Organic Chemistry, Jpn", vol 42, 794 (1984), and 7-fluoro-$PGI_2$ derivatives having fluorine introduced at the 7-position have been reported (Japanese Unexamined Patent Publications No. 171988/1982 and No. 243079/1985). Further, $PGI_2$ derivatives having a cycloalkyl group introduced to the ω-side chain in order to improve the pharmacological effect and stability, have been reported (Japanese Unexamined Patent Publication No. 163365/1984). However, there has been no report on $PGI_2$ having a cycloalkyl group introduced to the α-side chain or on derivatives thereof.

DISCLOSURE OF INVENTION

The present inventors have conducted extensive researches and as a result, have found that by introducing a cycloalkyl structure to the α-side chain of $PGI_2$ and introducing a halogen atom on the carbon atom corresponding to the 7-position of natural $PGI_2$, strong inhibitory activities on platelet aggregation and anti-anginal activities can be obtained, and yet these compounds have high stabilities. As the halogen atom, a fluorine atom is preferred, and the number is preferably one.

Thus, the present invention provides a novel prostaglandin $I_2$ derivative selected from a prostaglandin $I_2$ having a halogen atom on the carbon atom corresponding to the 7-position of natural prostaglandin $I_2$ and having a cycloalkylene group in the α-chain, and its esters and salts.

The present invention also provides a pharmaceutical composition for prophylaxis and treatment of circulatory diseases, which contains such a prostaglandin $I_2$ derivative as an active ingredient.

DETAILED DESCRIPTION OF THE INVENTION

In $PGI_2$ in the present invention, the bivalent hydrocarbon moiety in the α-chain corresponding to the trimethylene group at the 2- to 4-position of natural $PGI_2$ is preferably a $C_{3-8}$ cycloalkylene group, or a bivalent hydrocarbon group having a methylene group or a dimethylene group bonded to at least one bond of such a cycloalkylene group.

The hydrocarbon group corresponding to the n-pentyl group at the 16- to 20-position of natural $PGI_2$ is a monovalent organic group of various types, including an alkyl group, a substituted alkyl group, a cycloalkyl group, a substituted cycloalkyl group, an aryl group and a substituted aryl group. A alkyl group, a cycloalkyl-substituted alkyl group and a cycloalkyl group are preferred. Particularly, preferred is a $C_{5-8}$ linear or branched alkyl group.

In the present invention, preferred is a prostaglandin $I_2$ derivative of the following formula (I):

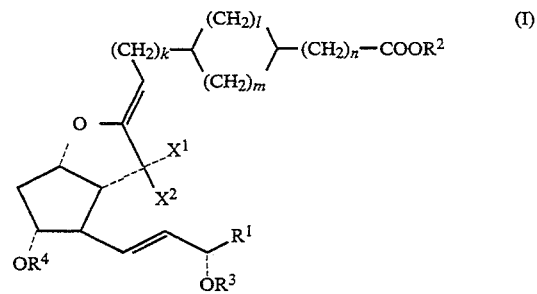

In the $PGI_2$ derivative of the formula (I) of the present invention, $R_1$ is a substituted or unsubstituted $C_{1-10}$ alkyl, alkenyl or alkynyl group, or a substituted or unsubstituted 5- or 6-membered cycloalkyl group. The $C_{1-10}$ alkyl, alkenyl or alkynyl group is preferably methyl, ethyl, n-propyl, iso-propyl, n-butyl, n-pentyl, n-hexyl, 1,1-dimethylpentyl, 2-methylhexyl, 1-methyl-3-pentenyl, 1-methyl-3-hexenyl, 1-methyl-3-pentynyl or 1-methyl-3-hexynyl. More preferably, it is a $C_{5-9}$ alkyl group. Particularly preferred among them is a n-pentyl group, a n-hexyl group, a 2-methylhexyl group or a 1,1-dimethylpentyl group.

The substituted or unsubstituted 5- or 6-membered cycloalkyl group is preferably a cyclopentyl group, or a cyclohexyl or cyclopentyl group substituted by e.g. methyl, ethyl, propyl, butyl, pentyl, phenoxy, trifluoromethyl or a trifluoromethylphenoxy.

$R^2$ is a hydrogen atom, a $C_{1-10}$ alkyl group or a cation.

This $C_{1-10}$ alkyl group may be a linear or branched alkyl group such as methyl, ethyl, n-propyl, iso-propyl, n-butyl, sec-butyl, tert-butyl, n-pentyl, n-hexyl, n-heptyl, n-octyl, n-nonyl or n-decyl. Among them, a methyl group and an ethyl group are preferred.

The cation may be an ammonium cation such as $NH_4^+$, tetramethyl ammonium, monomethyl ammonium, dimethyl ammonium, trimethyl ammonium, benzyl ammonium, phenethyl ammonium, morpholinium cation, monoethanol ammonium, tris cation or piperidinium cation; and alkali metal cation such as $Na^+$ or $K^+$; or a bivalent or trivalent metal cation such as $\frac{1}{2}Ca^{2+}$, $\frac{1}{2}Mg^{2+}$, $\frac{1}{2}Zn^{2+}$ or $\frac{1}{3}Al^{3+}$. Particularly preferred as $R^2$ is a methyl group or a sodium ion.

Each of $R^3$ and $R^4$ which may be the same or different, is a hydrogen atom or a protecting group. Various protecting groups may be employed. For example, a silyl group having three substitutents such as alkyl groups, aryl groups or aralkyl groups, an alkanoyl group, a tetrahydropyranyl group, a tetrahydrofuranyl group, a benzoyl group, or a methoxyethoxy group may be employed. Among them, a trialkylsilyl group is preferred, wherein the three alkyl groups may be the same or different, and particularly preferred is that at least one of the alkyl groups is an alkyl group having at least two carbon atoms. Specifically, a dimethyl-t-butylsilyl group, a triethylsilyl group or a diphenyl-t-butylsilyl group may, for example, be mentioned. Particularly preferred is a dimethyl-t-butylsilyl group.

One of $X^1$ and $X^2$ is a hydrogen atom, and the other is a halogen atom. The halogen atom is a fluorine atom or a chlorine atom. Particularly preferred is a fluorine atom. It is particularly preferred that $X^1$ is a fluorine atom, and $X^2$ is a hydrogen atom.

k, l, m and n are integers of from 0 to 6, provided that $1 \leq l+m \leq 6$ and $0 \leq k+n \leq 4$.

l and m represent numbers relating to the number of members constituting the ring of the cycloalkylene group and the position of the bonds of the cycloalkylene group. Namely, $l+m+2$ represents the number of carbon atoms consisting the ring of the cycloalkylene group. The smaller numerical value of l and m represents the positions of the bonds of the cycloalkylene group. For example, when the smaller of l and m is 0, such represents a 1,2-cycloalkylene group, and when the smaller of l and m is 1, such represents a 1,3-cycloalkylene group.

Each of k and n represents the number of methylene groups bonded to the bond of the cycloalkylene group. Each of k and n may be 0.

Each of l and m is preferably 0, 1, 2 or 3. Particularly preferably, $l+m$ is from 1 to 4. Namely, the cycloalkylene group is preferably from a cyclopropylene group to a cyclohexylene group. Each of k and n is preferably 0, 1 or 2. In this case, $k+n$ is preferably from 0 to 2. Particularly preferably, $k+n$ is 0 to 1.

Further, the length of the carbon chain corresponding to the trimethylene group at the 2- to 4-positions of natural PGI$_2$, i.e. each of $k+l+n+2$ and $k+m+n+2$, is preferably at most 6. Particularly preferably, the smaller of $k+l+n+2$ and $k+m+n+2$ is from 2 to 4, and the larger of them is from 3 to 5.

The compound of the formula (I) of the present invention has in its structure from 6 to 10 asymmetric carbon atoms and thus has various stereoisomers. The compound of the present invention includes all such stereoisomers, optical isomers and mixtures thereof.

The PGI$_2$ derivatives of the present invention can be synthesized by various methods. A feature of the PGI$_2$ derivative of the present invention resides in that it has a cycloalkylene group in the $\alpha$-chain. It can be prepared by a method for the preparation of otherwise known 7-haloPGI$_2$. Otherwise, it is also possible to employ usual methods for the preparation of PGI$_2$.

One of such methods is a method for preparing it by cyclization of the corresponding 7-haloPGF$_2\alpha$ or 7-halo-5,6-dehydroPGF$_2\alpha$ (5-, 6- and 7-positions represents positions corresponding to natural PGI$_2$, the same applies hereinafter) (for this method, please refer to Scheme 1 and its description given hereinafter). Further, there is a method wherein Corey lactone is used as a starting material for the synthesis. Further, it is also possible to synthesize PGI$_2$ having a cycloalkylene group in the $\alpha$-chain, followed by halogenation of the 7-position to obtain the PGI$_2$ derivative of the present invention.

When Corey lactone is used as a starting material for the preparation of the PGI$_2$ derivative of the present invention, it is usual to employ a method wherein the $\omega$-chain is firstly introduced, and then the $\alpha$-chain is introduced. However, the $\alpha$-chain may be introduced first. Introduction of the halogen atom may also be conducted at any optional order with respect to the introduction of these two chains. For the synthesis wherein Corey lactone is used as a starting material, there are a method wherein the halogen atom is introduced before the introduction of both the $\alpha$-chain and the $\omega$-chain, and then the remaining chains are introduced, and a method wherein the $\alpha$-chain and the $\omega$-chain are introduced first, and then the halogen atom is introduced (a method via 7-haloPGF$_2\alpha$ or 7-halo-5,6-dehydroPGF$_2\alpha$). For the former method, there are a method via 7-haloPGF$_2\alpha$ and a method not via 7-haloPGF$_2\alpha$.

Now, three embodiments (1) to (3) will be described for the method wherein Corey lactone is used as a starting material, and the $\omega$-chain is introduced first, followed by the introduction of the $\alpha$-chain. In these embodiments, the halogen atom is a fluorine atom.

(1) An $\omega$-chain-attached Corey lactone is fluorinated to obtain the corresponding fluoroketone. The fluorination may be conducted by a method wherein a hydroxyl group is firstly introduced to the carbon atom one which a fluorine atom is to be introduced, and then the fluorine atom is introduced by a fluorinating agent such as dimethylamino sulfur trifluoride, or by a method wherein the lactone is converted to an enolate, which is then reacted with XeF$_2$.

Then, an $\alpha$-chain is introduced to the fluoroketone. A basic reaction to introduce an $\alpha$-chain to a lactone by direct methylene conversion is known (T. Okazoe, K. Takai, K. Oshima, K. Utimoto, J. Org. Chem., 52, 4410, 1987), and this method can be employed. Further, it is also possible that a fluorolactone is reduced to a fluorochemiacetal, then an $\alpha$-chain is introduced by a Wittig reaction to obtain the after-mentioned compound (VII) (7-fluoroPGF$_2\alpha$), followed by cyclization as described hereinafter to obtain the desired product. For the Wittig reaction, reference may be made, for example, to E. J. Corey, N. M. Weinshenker, T. K. Schaaf, W. Huber, J. Am. Chem. Soc., 91, 5675, 1969.

(2) An $\omega$-chain-attached Corey lactone is reduced to a lactol, then an $\alpha$-chain is introduced by a Wittig reaction, and then a hydroxyl group is introduced at the 7-position to obtain the after-mentioned compound (VII). Thereafter, from the compound (VII), the desired compound can be prepared as will be described hereinafter.

(3) Cyclopentane carbaldehyde is prepared from a $\omega$-chain-attached Corey lactone (an $\omega$-chain-attached cyclopentanone may also be used as the starting material), and acetylide which will form an $\alpha$-chain, is reacted thereto to obtain 7-hydroxy-5,6-dehydroPGF$_2\alpha$. Then, this compound is fluorinated (see the fluorination in Scheme 1 given hereinafter) to obtain the after-mentioned compound (IV) (7-fluoro-5,6-dehydroPGF$_2\alpha$), from which the desired compound can be synthesized.

Now, a synthetic method via 7-haloPGF$_2\alpha$ or 7-halo-5,6-dehydroPGF$_2\alpha$, and a synthetic method for 7-haloPGF$_2\alpha$ or 7-halo-5,6-dehydroPGF$_2\alpha$ without using Corey lactone as a starting material, will be described in detail. In the description, the halogen atom at the 7-position is a fluorine atom.

The compound of the formula (I) of the present invention can be produced by the process represented by the following flow sheet (Scheme 1).

Scheme 1

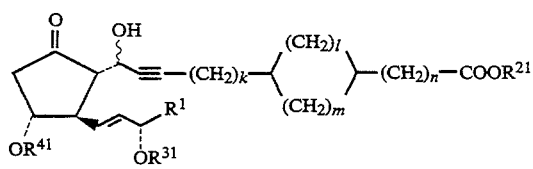
(II)

wherein $R^1$, k, l, m and n are as defined above with respect to the formula (I), $R^{21}$ is a $C_{1-10}$ alkyl group, and each of $R^{31}$ and $R^{41}$ which may be the same or different, is a protecting group other than a trimethylsilyl group.

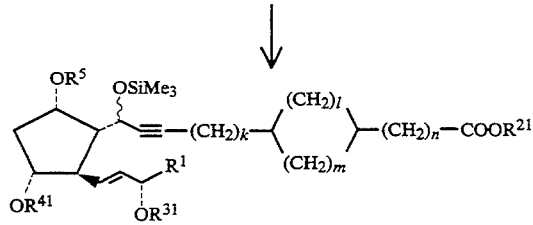
(III)

wherein $R^5$ is a protecting group different from $R^{31}$ and $R^{41}$ other than a trimethylsilyl group, and $R^1$, $R^{21}$, $R^{31}$, $R^{41}$, k, l, m and n are as defined above with respect to the formula (II).

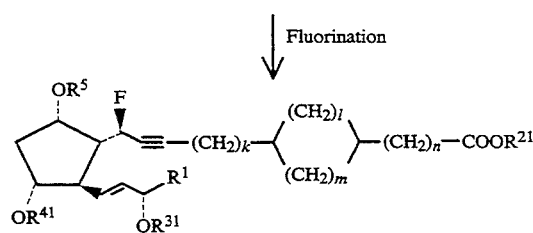
(IV)

Wherein $R^1$, $R^{21}$, $R^{31}$, $R^{41}$, $R^5$, k, l, m and n are as defined above with respect to the formula (III).

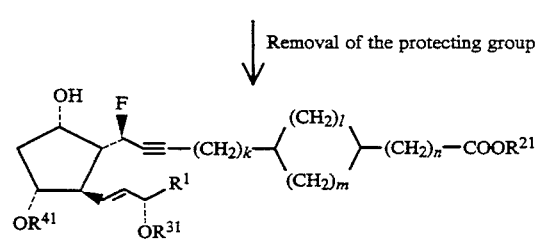
(V)

Wherein $R^1$, $R^{21}$, $R^{31}$, $R^{41}$, k, l, m and n are as defined above with respect to the formula (II).

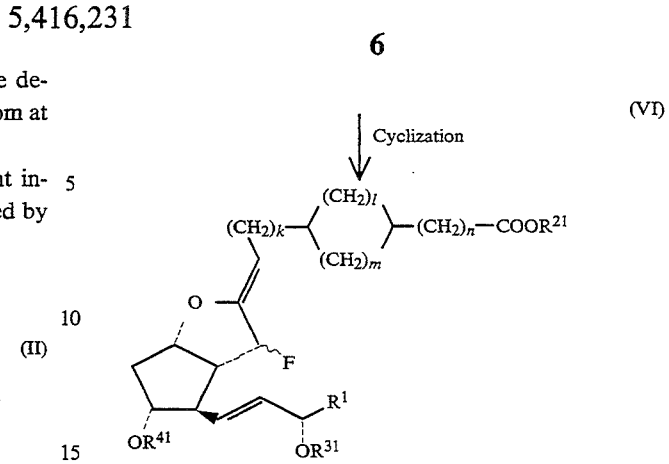
(VI)

Wherein $R^1$, $R^{21}$, $R^{31}$, $R^{41}$, k, l, m and n are as defined above with respect to the formula (II).

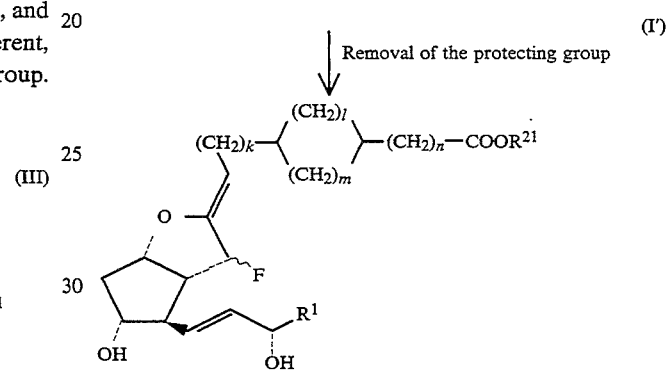
(I')

Wherein $R^1$, $R^{21}$, k, l, m and n are as defined above with respect to the formula (II).

Namely, the compound of the formula (II) is converted to the compound (III) by the method disclosed in the applicants' earlier application (Japanese Unexamined Patent Publication No. 10551/1986), followed by fluorination (compound (IV)), removal of a protecting group (compound (V)), cyclization (compound (VI)), removal of a protecting group and, if desired, hydrolysis or salt-formation, whereby the compound of the above formula (I') can be obtained. In the above formula (III), $R^5$ is a tri($C_{1-7}$)hydrocarbonsilyl group other than a trimenthysilyl group, or a group capable of forming an acetal bond together with the oxygen atom of the hydroxyl group. As the tri($C_{1-7}$)hydrocarbonsilyl group, a triethylsily group is particularly preferred. As the group capable of forming an acetal bond together with the oxygen atom of the hydroxyl group, a 2-tetrahydropyranyl group or a 2-tetrahydrofrany group is particularly preferred. Each of $R^{31}$ and $R^{41}$ is a protecting group different form $R^5$ other than a trimethylsilyl group and is preferably a tri($C_{1-7}$)hydrocarbonsilyl group. As the tri($C_{1-7}$)hydrocarbonsilyl group, a tri($C_{1-4}$)alkylsilyl group such as a t-butyldimethylsilyl, a diphenyl($C_{1-4}$)alkylsilyl group such as a t-butylidiphenylsilyl group, or a tribenzylsilyl group may, for example, be mentioned as a preferred group, Particularly preferred is a t-butyldimethylsilyl group. The fluorination of the compound (III) can be conducted by a known method (Japanese Unexamined Patent Publications No. 32718/1985 and No. 227888/1984). Namely, it can preferably be conducted by an amino surfer trifluoride type fluorinating agent such as piperidino sulfur trifluoride or diethylamino sulfur trifluoride in a fluorinated hydrocarbon type solvent such as 1,1,2-trichloro-1,2,2-trifluoroethane or trichlorofluoromethane. By the reaction with such fluorinating agent, a compound of the formula (IV) is obtained, and such a compound can be converted to a compound of the formula (V) by a known reaction for removal of a protecting group. The removal of a protecting group can suitably be conducted by using e.g. acetic acid, p-toluene sulfonic acid, pyridinium p-toluene sulfonate or a cation exchange resin, as a catalyst, and using e.g. water, methanol or ethanol, or tetrahydrofuran, ethyl ether, dioxane, acetone or acetonitrile in the presence of water, methanol, ethanol or the like, as the solvent for reaction. The reaction is conducted usually within a temperature range of from $-78°$ C. to $+50°$ C. for from 10 minutes to 3 days. The compound of the formula (V) can be converted to a compound of the formula (VI) by a cyclization reaction. For this cyclization reaction, a known technique can basically be employed. For example, it can be conducted in accordance with a method disclosed in J. Amer. Chem. Soc., vol 104, p 5842–5844 (1982). Namely, the cyclization reaction can be conducted by cyclization by means of mercury trifluoroacetate, followed by hydrogenation with a hydrogenating agent. Otherwise, it can be conducted in accordance with the method disclosed in Japanese Unexamined Patent Publication No. 120377/1987. Namely, the cyclization reaction can be conducted by cyclization by means of phenyl selenenyl chloride, followed by removal of the phenyl selenenyl group by means of a reducing agent such as tributyltin hydride. Otherwise, it can also be conducted in accordance with the method disclosed in U.S. Pat. No. 4,612,380. Namely, the cyclization reaction can be conducted by hydrogenating the compound of the formula (V) by a known method (Tetrahedron Letters, vol 25, p 1383–1386 (1984)) to convert it to a compound of the following formula (VII):

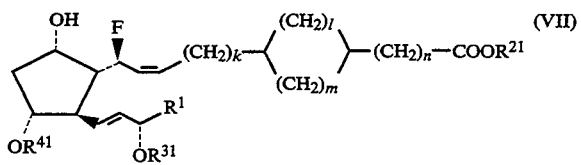

wherein $R^1$, $R^2$, $R^3$, $R^{21}$, $R^{31}$, $R^{41}$, k, l, m and n are as defined above, and cyclizing it by means of N-iodosuccinic acid imide or iodine, followed by removal of hydrogen iodide by means of a base such as 1,8-diazabicyclo[5,4,0]-7-undecene (DBU). The compound of the formula (VI) thus obtained may be subjected to a reaction for removal of a protecting group and/or a hydrolyzing reaction and/or an esterification reaction and/or a salt-forming reaction, as in the case requires, to obtain a prostaglandin $I_2$ derivative (I') of the present invention. For the removal of a protecting group for the hydroxyl group (the reaction for removal of a protecting group), a fluorine-type reagent such as tetrabutyl ammonium fluoride, cesium fluoride, hydrofluoric acid or hydrogen fluoride/pyridine can be used. Tetrabutyl ammonium fluoride is particularly preferred. As the solvent for reaction, tetrahydrofuran, ethyl ether, dioxane, acetone or acetonitrile can, for example, be used. The reaction can suitably be conducted usually within a temperature range of from $-78°$ C. to $+50°$ C. for from 10 minutes to 3 days. The reaction for hydrolysis of the ester group at the 1-position can be conducted by a usual method, for example by hydrolyzing it with an aqueous solution or a water-alcohol mixture solution of e.g. sodium hydroxide, potassium hydroxide or calcium hydroxide, or with an alcohol-water mixture solution containing sodium methoxide, postassium methoxide or sodium ethoxide. Otherwise, the hydrolysis may be conducted by treatment with an enzyme such as lipase in water or in a solvant containing water within a temperature range of from $-10°$ C. to $+60°$ C. for from 10 minutes to 24 hours. Post treatment and purification after the hydrolytic reaction can be conducted in a usual manner after neutralization with an acid such as dilute hydrochloric acid or oxalic acid.

The compound having a carboxyl group formed by the above mentioned hydrolytic reaction is then further subjected to a salt-forming reaction, as the case requires, to obtain the corresponding carboxylate. The salt-forming reaction is known per se and can be conducted by subjecting the carboxylic acid and a substantially equivalent amount of a basic compound such as sodium hydroxide, potassium hydroxide or sodium carbonate, or ammonia, trimethylamine, monoethanol amine or morpholine, to a neutralization reaction by a usual method. The carboxylate can directly be obtained by the above-mentioned reaction for hydrolysis of the ester.

The esterification of the hydroxyl group can readily be accomplished by a usual method of reacting an acid anhydride or an acid halide in the presence of a base, i.e. by reacting acetic anhydride, acetyl chloride or benzoyl chloride in the presence of a base such as pyridine or triethylamine (Shinjikken Kagaku Koza, vol 14-II, 1002–1027, compiled by Japan Chemical Association, Maruzen K.K.).

There is no particular restriction as to the method for preparing the compound of the formula (II) which is the starting material of the present invention. However, it can be prepared, for example, by two methods (a) and (b) shown in the following Scheme 2.

Scheme 2

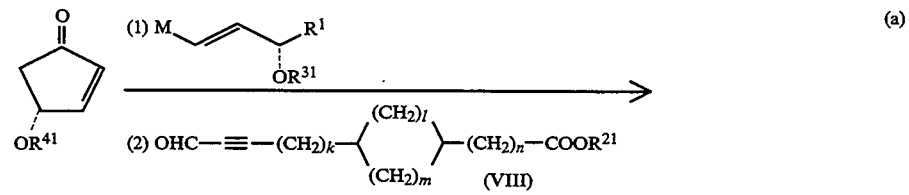

(a)

Scheme 2

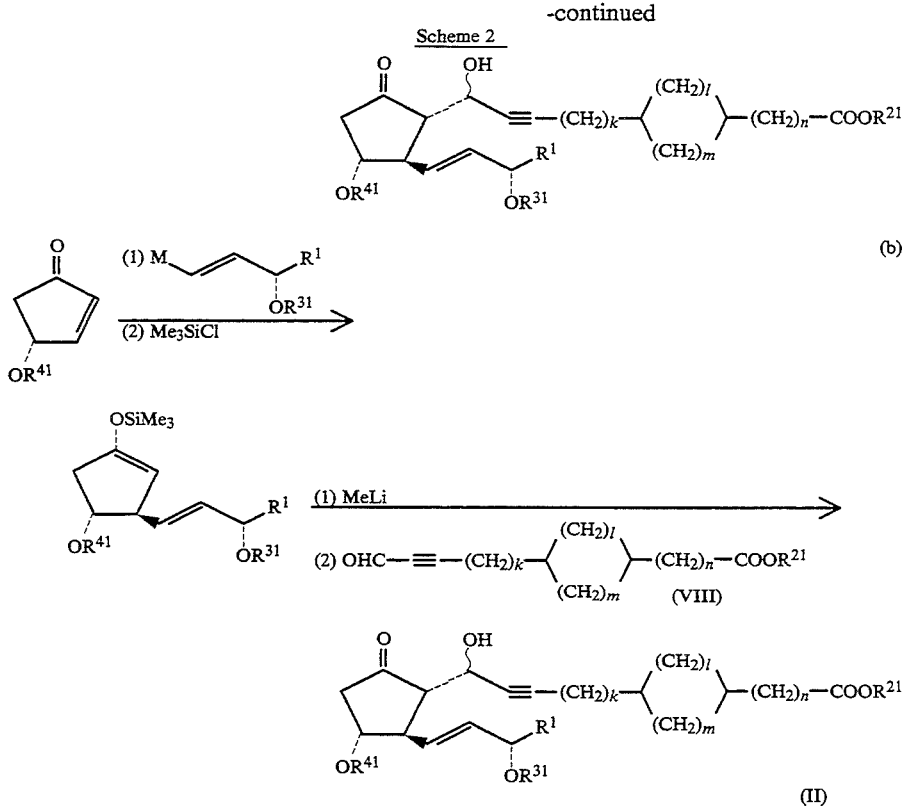

(b)

wherein M is an organic metal species (such as copper, nickel, zirconium, zinc or aluminum), and $R^1$, $R^{21}$, $R^{31}$, $R^{41}$, k, l, m and n are as defined above with respect to the formula (II).

Here, the method (a) can be conducted in accordance with the method disclosed in Tetrahedron Letters, vol 23, 4057 (1982). In (b), the method of conducting 1,4-addition of an alkenyl metal reactant to an enone and capturing it with a trimethylsilyl group is known (J. Am. Chem. Soc., vol 97, 107 (1975)), and the obtained silylether can be converted to a compound of the formula (II) in accordance with a known technique (J. Am. Chem. Soc., vol 95, 3310 (1973)). The aldehyde of the formula (VIII) used here, is a novel compound. There is no particular restriction as to the method for preparing this compound. However, this compound can be prepared by the method shown in the following flow chart (Scheme 3).

Scheme 3

(a) In a case where each of k and n in the formula (VIII) is 0:

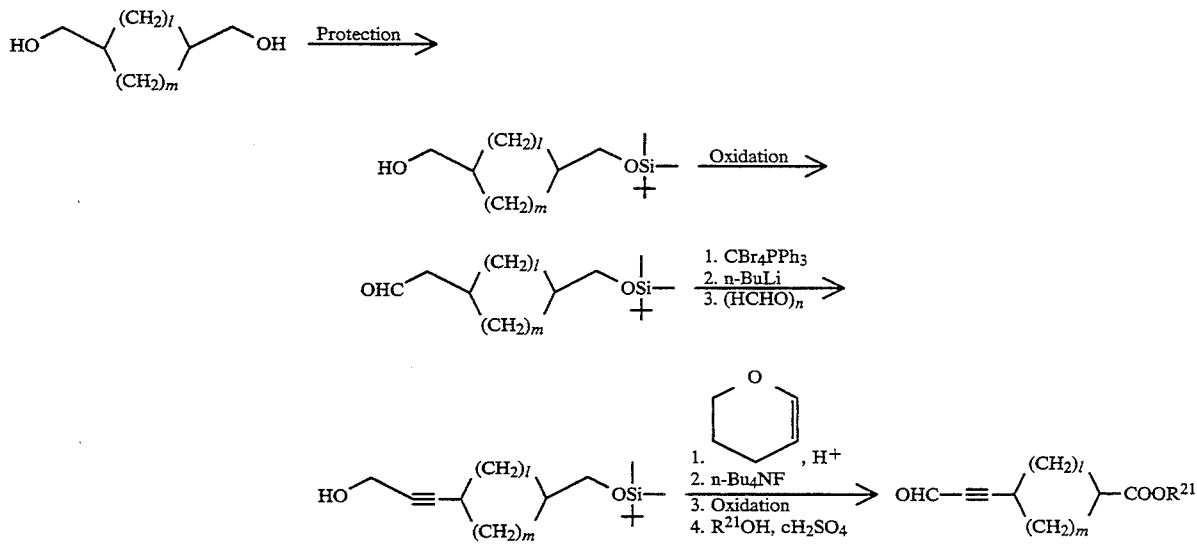

(b) In a case where in the formula (VIII), k is 0 and is 1:

-continued
Scheme 3

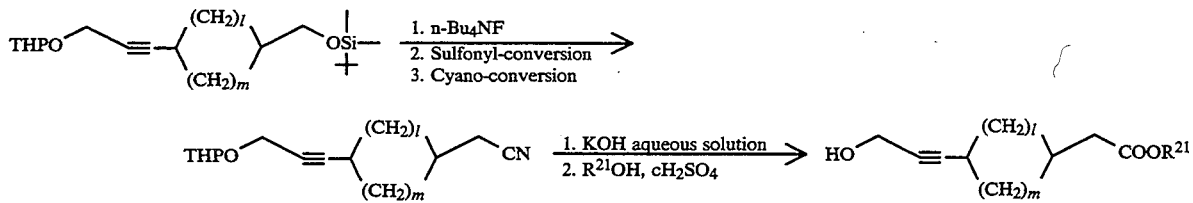

(c) In a case where in the formula (VIII), k is 2, l is 1 and each of m and n is 0:

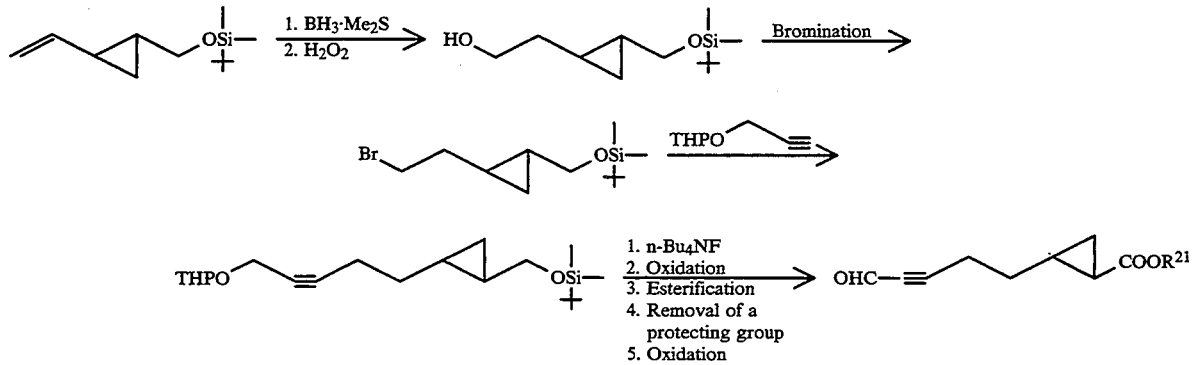

(d) In a case where in the formula (VIII), each of k and l is 1, and each of m and n is 0:

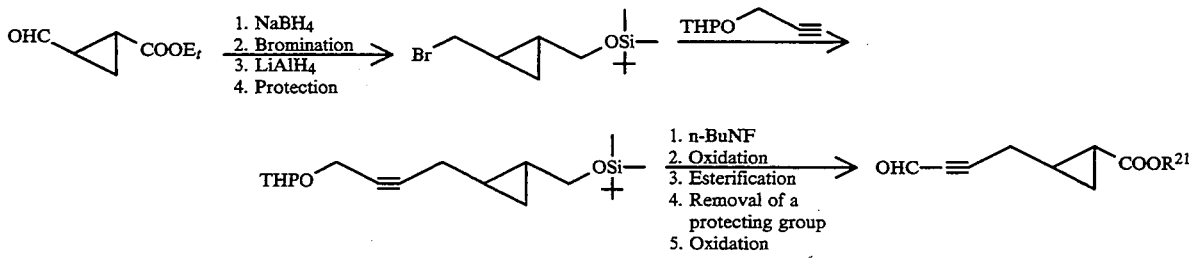

(e) In a case where in the formula (VIII), each of k an n is 0, l is 1, and m is 2:

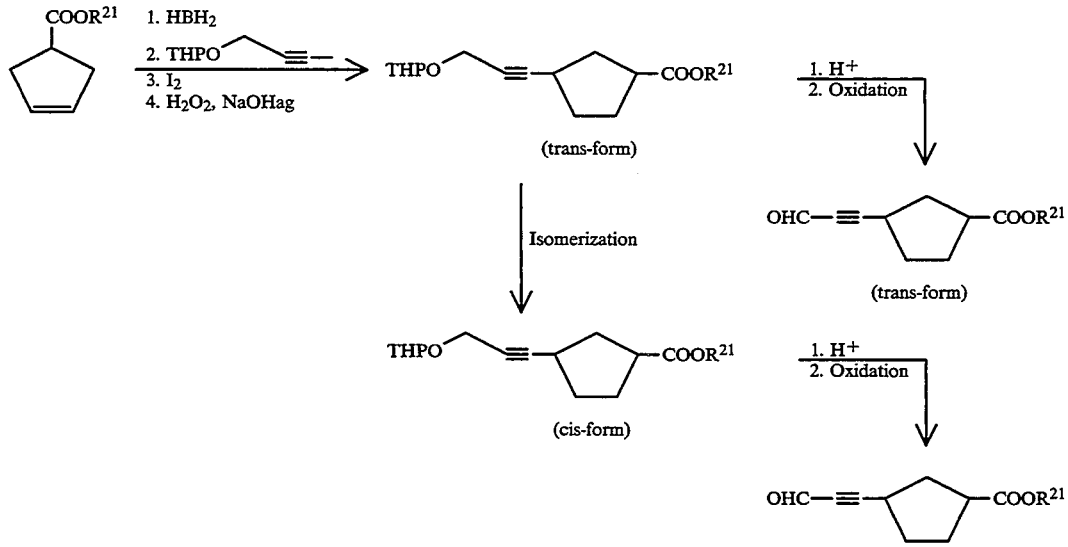

Compounds (I) of the present invention and their salts have strong anti-platelet inhibitory activities and anti-anginal activities, and yet their toxicity is weak. Therefore, they are useful for prevention and treatment of e.g.

thrombosis, angina pectoris, cardiac infarction, or arterial sclerosis.

Pharmacological test results of the compounds of the present invention are as follows.

Inhibitory activities on platelet aggregation

From a guinea pig (Hartley strain), citric acid-added blood was obtained by a cardiac puncture. The blood was centrifuged at 120×g for 10 minutes, and the supernatant platelet rich plasma was separated. Measurement of platelet aggregation was conducted by means of an aggregometer in accordance with the Bone's nephelometry (G. V. R. Bone; Nature, vol 194, p 927, 1962). In a test in vitro, a test compound was added to the platelet rich plasma, and the mixture was incubated for 10 minutes. Then, adensoine diphosphate (1 micro M) was added to induce platelet aggregation. The degree of aggregation was represented by the maximum change in the light transmittance (the maximum aggregation rate) within 5 minutes after the addition of adenosine diphosphate, and the results are shown by a 50% inhibitory concentration. In a test ex vivo, a test compound was dissolved in ethanol, then suspended in a 0.5% tragacanth solution or in a 1% β-cyclodextrin solution and orally administered. From blood obtained by a cardiac puncture 30 minutes after the administration, a platelet rich plasma was prepared, and platelet aggregation was measured in the same manner as in the case of the test in vitro. The results are shown in Table 1.

In Table 1 and subsequent Tables, the following abbreviations are used to represent compounds and solvents. Further, as a reference compound, the compound F (natural prostagrandin $I_2$) was used.

Compound A: sodium salt of 2,3-methylene-7α-fluoro-17,20-dimethylPGI$_2$ prepared in Example 1

Compound B-b: high polarity isomer of methyl ester of (1S*,3S*)-2,4-ethylene-7α-fluoro-17,20-dimethylPGI$_2$ prepared in Example 3

Compound C: methyl ester of (1S*,3R*)-2,4-ethylene-7α-flouro-17,20-dimethylPGI$_2$ prepared in Example 4

Compound D-a: low polarity isomer of methyl ester of 2,4-methylene-7α-fluoro-17,20-dimethylPGI$_2$ prepared in Example 7

Compound D-b: high polarity isomer of methyl ester of 2,4-methylene-7α-fluoro-17,20-dimethylPGI$_2$ prepared in Example 7

Compound E-a: low polarity isomer of sodium salt of 2,4-methylene-7α-fluoro-17,20-dimethylPGI$_2$ prepared in Example 7

Compound E-b: high polarity isomer of sodium salt of 2,4-methylene-7α-fluoro-17,20-dimethylPGI$_2$ prepared in Example 7

Compound F: natural PGI$_2$

Solvent X: 0.5% tragacanth solution

Solvent Y: 1% β-cyclodextrin solution

TABLE 1

| Compound | in vitro IC$_{50}$ (ng/ml) | ex vivo MED (mg/kg) | Solvent |
|---|---|---|---|
| Compound A | 18.3 | — | X |
| Compound B-b | 0.87 | 0.3 | X |
| Compound C | 5.50 | — | X |
| Compound D-a | 2.88 | 0.3 | Y |
| Compound D-b | 1.50 | 0.3 | Y |
| Compound E-a | 1.13 | — | Y |
| Compound E-b | 1.70 | 0.3 | Y |
| Compound F | — | >10 | Y |

MED: Minimum effective dose showing significant inhibitory effects (P < 0.05)

As is apparent from the above Table, compounds of the present invention have strong anti-platelet activities.

Anti-anginal activities (Preventive activities on vasopressin-induced ST depression)

Vasopressin (0.2 IU/kg) was administered from the femoral vein of a male rat (Donryou strain) anesthetized with pentobarbital, and the electrocardiogram was recorded for 5 seconds each at intervals of 30 seconds over a period of 5 minutes after the administration. The depression of ST-segment (the average of five pulses) was calculated on the electrocardiogram. The test compound was dissolved in ethanol and intravenously administered 2 minutes prior to the administration of vasopressin, or after being dissolved in ethanol, suspended in a 0.5% tragacanth solution or in a 1% β-cyclodextrin solution and orally administered 30 minutes prior to the administration of vasopressin. The differences of the ST depression between the test compound-administered group and the non-treated control group (5 animals for each group) were analysed by two-way layout analysis of variance. The results are shown in Table 2.

TABLE 2

| Compound | Intravenous administration MED (μ/kg) | Oral administration MED (mg/kg) | Solvent |
|---|---|---|---|
| Compound B-b | 1.0 | 0.01 | X |
| Compound D-b | — | 0.1 | Y |
| Compound E-a | 1.0 | 0.1 | Y |
| Compound E-B | 1.0 | 0.1 | Y |

MED: Minimum effective dose showing a significant preventive activity (P < 0.05)

As shown in the above Table, compounds of the present invention have strong anti-anginal activities.

Acute toxicity

To male mice of ddY strain weighing 25–32 g (five animals per each group), a predetermined dose of a test compound dissolved in a small amount of ethanol and then diluted with a 1% β-cyclodextrin solution, was orally administered, and the mortality was recorded over a period of 7 days after the administration. The results are shown in Table 3.

TABLE 3

| Compound | Dose (mg/kg) | Number of dead animals/ Number of test animals |
|---|---|---|
| Compound D-b | 20 | 0/5 |
| Compound E-b | 20 | 0/5 |

As shown in Table 3, the toxicity of the compounds of the present invention is very low.

The compound of the present invention may be administered orally or parenterally such as subcutaneously, intramuscularly, intravenously, percutaneously or intrarectally. Compositions for oral administration may be solid compositions such as tablets, granules, powders or capsules, or liquid compositions such as emulsions, solutions, suspensions, syrups or elixirs. The tablets may be formed by a usual method employing an excipient such as lactose, starch, crystalline cellulose or polyvinyl pyrrolidone; a binder such as carboxymethyl cellulose or methyl cellulose; and a disintegrator such as sodium alginate, sodium hydrogen carbonate or sodium lauryl sulfate. The granules and powders can likewise be formed by usual methods by means of e.g. the above excipients. Capsules can be prepared, for example, by filling a solution obtained by dissolving the compounds of the present invention in a vegetable oil such as coconut oil, into gelatin soft capsules.

Compositions for non-oral administration may be sterile aqueous or non-aqueous solutions, suspensions or emulsions, or sterile solid compositions to be dissolved in sterile injectable medium immediately before use. Further, a suppository for intrarectal administration or a pessary for administration in vagina may be administered.

The compound of the present invention may be used for formulation in the form of a clathrate compound with α-, β- or γ-cyclodextrin, or methylated cyclodextrin.

A daily dose of the compound of the present invention is usually from 0.0001 to 1.0 mg/kg. It is preferably from 0.0001 to 0.3 mg/kg in the case of intramuscular, subcutaneous or intravenous administration and from 0.0001 to 1.0 mg/kg in the case of oral administration. However, the dose varies depending upon the age and weight of the patient, the degree of disease, the type of disease and the number of administrations, and it is not restricted to the above ranges.

Now, the present invention will be described in further detail with reference to Reference Examples, Working Examples and Preparative Examples. However, it should be understood that the present invention is by no means restricted to such specific Examples.

REFERENCE EXAMPLE 1

Preparation of 2-bromomethylcyclopropanecarboxylic acid ethyl ester (2-formyl)cyclopropanecarboxylic acid ethyl ester (14.2 g, 0.10 mol) was dissolved in methanol (200 ml). The solution was cooled to 0° C., and sodium borohydride (3.8 g, 0.10 mol) was added. The mixture was stirred for 20 minutes. After distilling off the solvent, a saturated sodium chloride aqueous solution was added thereto. The product was extracted with chloroform, then dried and concentrated. Then, it was purified by silica gel column chromatography (hexane:ethyl acetate=2:1) to obtain (2-hydroxymethyl)cyclopropanecarboxylic acid ethyl ester (14.3 g, yield: 99%).

The (2-hydroxymethyl)cyclopropanecarboxylic acid ethyl ester (14.3 g, 0.1 mol) was dissolved in N,N-dimethylformamide (150 ml), and triphenylphosphine (25.9 g, 0.1 mol) was added thereto at room temperature. The mixture was stirred for 10 minutes. After cooling the mixture to 20° C., bromine (15.8 g, 0.1 mol) was dropwise added thereto over a period of 10 minutes. One hour later, the reaction mixture was added to a saturated sodium hydrogen carbonate solution, and the product was extracted with ethyl ether. It was dried, concentrated and then purified by column chromatography (hexane:ethyl acetate=5:1) to obtain (2-bromomethyl)cyclopropane carboxylic acid ethyl ester (15.3 g, yield: 74%).

$^1$NMR(CDCl$_3$) δ0.9–1.0(m, 1H), 1.27(t, J=7.6 Hz, 3H), 1.3–1.5(m, 1H), 1.6–1.7(m, 1H, 1.8–2.0(m, 1H), 3.3–3.4(m, 2H), 4.25(q, J=7.6 Hz, 2H)

REFERENCE EXAMPLE 2

Preparation of 2-bromomethylcyclopropylmethanol

The (2-bromomethyl)cyclopropanecarboxylic acid ethyl ester (15.3 g, 74 mmol) was dissolved in ethyl ether (50 ml) and then added to a suspension of lithium aluminum hydride (2.8 g, 74 mmol) in ethyl ether (150 ml). The mixture was stirred at room temperature for one hour. Then, 2N hydrochloric acid was added thereto, and the product was extracted with ethyl ether, dried and concentrated. It was then purified by column chromatography to obtain (2-bromomethyl)cyclopropylmethanol (6.7 g, yield: 55%).

$^1$H-NMR (CDCl$_3$) δ0.6–0.7(m, 1H), 07.–0.8(m, 1H), 1.0–1.2(m, 2H), 1.7–1.8(m, 1H), 3.2–3.6(m, 4H)

REFERENCE EXAMPLE 3

Preparation of 2-bromomethylcyclopropylmethyl t-butyldimethylsilyl ether

The (2-bromomethyl)cyclopropylmethanol (6.7 g, 41 mmol) was dissolved in N,N-dimethylformamide (80 ml), and imidazole (6.8 g, 0.1 mol) and t-butyldimethylsilyl chloride (9.0 g, 60 mmol) was added thereto at 0° C. The mixture was stirred for one hour. Then, water was added thereto, and the product was extracted with ethyl ether, then dried and concentrated. Then, it was purified by silica gel column chromatography to obtain (2-bromomethyl)cyclopropylmethyl t-butyldimethylsilyl ether (10.5 g, yield: 92%).

$^1$N-NMR(CDCl$_3$) δ0.08(s, 6H), 0.5–0.6(m, 1H), 0.7–0.8(m, 1H), 0.92(s, 9H), 1.0–1.1(m, 1H), 1.2–1.3(m, 1H), 3.3–3.4(m, 2H), 3.56(d, J=5.6 Hz, 2H)

REFERENCE EXAMPLE 4

Preparation of 2-(4-tetrahydropyranyloxy-2-butynyl)cyclopropylmethyl t-butyldimethylsilyl ether Propargyl alcohol tetrahydropyranyl ether (5.6 g, 40 mmol) was dissolved in tetrahydrofuran (80 ml), and the solution was cooled to −78° C. Butyllithium (27 ml, factor=1.48, 40 ml) was added thereto. Fifteen minutes later, the temperature was raised to 0° C. Ten minutes later, hexamethylphosphoric triamide (14.3 g, 80 mmol) was added thereto, and a tetrahydrofuran solution (20 ml) of (2-bromomethyl)cyclopropylmethyl t-butyldimethylsilyl ether (11.2 g, 40 mmol) was added thereto. The mixture was stirred at 0° C. for one hour and at room temperature for 3 hours. Water was added thereto, and the product was extracted with ethyl ether, then dried and concentrated. Then, it was purified by silica gel column chromatography to obtain 2-(4-tetrahydropyranyloxy-2-butynyl)cyclopropylmethyl t-butyldimethylsilyl ether (5.8 g, yield: 43%).

$^1$N-NMR(CDCl$_3$) δ0.00(s, 6H), 0.4–0.5(m, 1H), 0.8–1.0(m, 3H), 0.86(s, 9H), 1.4–1.9(m, 6H), 2.2–2.3(m, 2H), 3.4–3.5(m, 3H, 3.8–3.9(m, 1H), 4.15(d, J=14 Hz, 1H), 4.23(d, J=14 Hz), 1H), 4.7–4.8(m, 1H)

REFERENCE EXAMPLE 5

Preparation of 2-(4-hydroxy-2-butynyl)cyclopropanecarboxylic acid methyl ester

The 2-(4-tetrahydropyranyloxy-2-butynyl)cyclopropylmethyl t-butyldimethylsilyl ether (5.8 g, 17.2 mmol) was dissolved in tetrahydrofuran (50 ml), and a tetrabutyl ammonium fluoride (factor=1.0) tetrahydrofuran solution (33 ml, 33 mmol) was added thereto at 0° C. The mixture was stirred for one hour. The product was purified by column chromatography to obtain 2-(4-tetrahydropyranyloxy-2-butynyl)cyclopropylmethanol (4.3 g).

The 2-(4-tetrahydropyranyloxy-2-butynyl)cyclopropylmethanol (4.3 g) was dissolved in acetone (30 ml) and then oxidized to a cyclopropanecarboxylic acid with a John's reagent at 0° C.

The crude product was dissolved in ethyl ether (50 ml) and methyl-esterified with diazomethane. The reaction solution was concentrated, and the crude product was dissolved in ethanol (30 ml). Then, pyridinium p-toluenesulfonate (0.5 g) was added thereto, and the mixture was heated to 50° C. and stirred for 1.5 hours. Then, a saturated sodium hydrogen carbonate solution was added thereto, and the product was extracted with dichloromethane. It was dried over anhydrous magnesium salfate, concentrated and then purified by silica gel column chromatography to obtain 2-(4-hydroxy-2-butynyl)cyclopropane carboxylic acid methyl ester (0.7 g).

$^1$N-NMR(CDCl$_3$) δ0.9–1.0(m, 1H), 1.1–1.3(m, 1H), 1.5–1.7(m, 1H), 1.8–1.9(m, 1H), 2.4–2.5(m, 2H), 3.64(s, 3H), 4.22(s, 2H)

REFERENCE EXAMPLE 6

Preparation of 2-(4-oxo-2-butynyl)cyclopropanecarboxylic acid methyl ester

Oxalyl chloride (0.78 g, 6.2 mmol) was dissolved in dichloromethane (12 ml), and the solution was cooled to −40° C. A solution of dimethylsufloxide (1.0 g, 12.3 mmol) in dichloromethane (4 ml) was dropwise added thereto over a period of 10 minutes. Fifteen minutes later, a solution of 2-(4-hydroxy-2-butynyl)cyclopropanecarboxylic acid methyl ester (0.70 g, 4.1 mmol) in dichloromethane (5 ml) was dropwise added thereto over a period of 15 minutes. Forty minutes later, triethylamine (2.5 g, 25 mmol) was added thereto, and the temperature was raised to 0° C. Water was added thereto, and the product was extracted with dichloromethane, and the crude product thereby obtained was roughly separated by silica gel column chromatography to obtain 2-(4-oxo-2-butynyl)cyclopropanecarboxylic acid methyl ester (0.32 g).

REFERENCE EXAMPLE 7

Preparation of 2-(2-hydroxyethyl)cyclopropylmethyl t-butyldimethylsilyl ether 2-vinylcyclopropylmethyl t-butyldimethylsilyl ether (17.1 g, 81 mmol) was dissolved in tetrahydrofuran (100 ml) and cooled to 0° C. A borane-dimethylsulfide complex (2.5 g, 33 mmol) was added thereto, and the mixture was stirred for one hour. Ethanol (38 ml), 3N sodium hydroxide (38 ml) and 30% hydrogen peroxide (18.2 ml) were added thereto, and the mixture was stirred for 30 minutes. The saturated sodium chloride aqueous solution was added thereto, and the product was extracted with ethyl acetate, then dried over anhydrous magnesium sulfate and concentrated. Then, it was purified by silica gel column chromatography to obtain 2-(2-hydroxyethyl)cyclopropylmethyl t-butyldimethylsilyl ether (15.0 g, yield: 81%).

$^1$N-NMR(CDCl$_3$) δ0.00(s, 3H), 0.05(s, 3H), 0.3–0.4(m, 2H), 0.5–0.6(m, 1H), 0.91(s, 9H), 0.9–1.0(m, 1H), 1.1–1.2(m, 1H), 1.81(dq, J=14.0, 4.7 Hz, 1H), 3.03(dt, J=9.4, 10.3 Hz, 1H), 3.71(d, J=4.2 Hz, 1H), 3.75(d, J=4.2 Hz, 1H), 3.94(dd, J=10.3, 5.1 Hz, 1H)

REFERENCE EXAMPLE 8

Preparation of 2-(5-tetrahydropyranyloxy-3-pentynyl)cyclopropylmethyl t-butyldimethylsilyl ether 2-(2-hydroxyethyl)cyclopropylmethyl t-butyldimethylsilyl ether (15.0 g, 65 mmol) was dissolved in N,N-dimethylformamide (120 ml), and triphenylphosphine (17.3 g, 66 mmol) was added thereto at room temperature. Twenty minutes later, the mixture was cooled to −20° C. Bromine (10.5 g, 66 mmol) was added thereto over a period of 5 minutes, and the temperature was gradually raised to 0° C. The mixture was poured into a saturated sodium hydrogen carbonate aqueous solution, and the product was extracted with ethyl ether. Then, it was dried over anhydrous magnesium sulfate and purified by silica gel column chromatography to obtain 2-(2-bromoethyl)cyclopropylmethyl t-butyldimethylsilyl ether (2.7 g).

A tetrahydrofuran solution (15 ml) of propargyl alcohol tetrahydropyranyl ether (1.44 g, 10.3 mmol) was cooled to −78° C., and butyllithium (factor=1.5, 6.9 ml, 10.3 mmol) was added thereto. Fifteen minutes later, the temperature was raised to 0° C. Hexamethylphosphoric triamide (3.76 ml, 21 mmol) was added thereto, and the mixture was stirred for 15 minutes. A tetrahydrofuran solution of 2-(2-bromoethyl)cyclopropylmethyl t-butyldimethyl silyl ether (2.73 g, 10.3 mmol) was added thereto, and the mixture was stirred at room temperature for 2 hours. A saturated ammonium chloride solution was added thereto, and the product was extracted with ethyl ether. The crude product was purified by silica gel column chromatography to obtain 2-(5-tetrahydropyranyloxy-3-pentynyl)cyclopropylmethyl t-butyldimethylsilyl ether (3 g).

$^1$N-NMR(CDCl$_3$) δ0.00(s, 6H), 0.2–0.3(m, 1H), 0.3–0.4(m, 1H), 0.6–0.7(m, 1H), 0.7–0.8(m, 1H), 0.87(s, 9H), 1.4–1.9(m, 8H), 2.2–2.3(m, 2H), 3.4–3.5(m, 3H), 3.7–3.9(m, 1H), 4.14(d, J=14.0 Hz, 1H), 4.26(d, J=14.0 Hz, 1H), 5.76(t, J=3.7 Hz, 1H).

REFERENCE EXAMPLE 9

Preparation of 2-(5-tetrahydropyranyloxy-3-pentynyl)cyclopropylmethanol

The 2-(5-tetrahydropyranyloxy-3-pentyl)cyclopropylmethyl t-butyldimethylsilyl ether (3 g, 10 mmol) was dissolved in tetrahydrofuran (10 ml), and tetrabutyl ammonium fluoride (factor=1.0, 12 ml, 12 mmol) was added at 0° C. The mixture was stirred for 30 minutes. The solvent was distilled off, and the product was purified by silica gel column chromatography to obtain 2-(5-tetrahydropyranyloxy-3-pentynyl)cyclopropanemethanol (1.2 g)

$^1$N-NMR(CDCl$_3$) δ0.2–0.4(m, 2H), 0.6–0.8(m, 1H), 0.88(t, J=7.5 Hz, 1H), 1.1–1.9(m, 8H), 2.2–2.4(m, 2H), 3.3–3.6(m, 3H), 3.7–3.9(m, 1H), 4.14(d, J=15 Hz, 1H), 4.27(d, J=15 Hz, 1H), 4.76(s, 1H)

REFERENCE EXAMPLE 10

Preparation of 2-(5-hydroxy-3-pentynyl)cyclopropanecarboxylic acid methyl ester

The alcohol (0.70 g, 2.9 mmol) prepared in Reference Example 9 was dissolved in dichloromethane (30 ml), and pyridinium chlorochromate (0.90 g) was added thereto. The mixture was stirred at room temperature for 6 hours. The reaction mixture was filtered through Celite and concentrated to obtain an aldehyde (0.62 g).

To the above aldehyde (0.62 g), a mixture comprising a solution of silver nitrate (2 g) in water (4 ml) and a solution of sodium hydroxide (0.93 g) in water (4 ml), was added at 0° C., and the mixture was stirred for 5 minutes. The mixture was filtered through Celite and adjusted to pH7 with concentrated hydrochloric acid. The solvent was distilled off, and the residue was dissolved in ethyl ether (3 ml) and methyl-esterified by an addition of diazomethane-ethyl ether solution. The product was purified by silica gel column chromatography to obtain a methyl ester compound (0.46 g).

The above methyl ester compound (0.45 g, 1.5 mmol) was dissolved in ethanol (30 ml), and pyridinium p-toluenesulfonate (80 mg, 0.3 mmol) was added thereto. The mixture was stirred at 60° C. for 2 hours. The product was purified by silica gel column chromatography to obtain the above identified compound (0.31 g).

$^1$N-NMR(CDCl$_3$) $\delta$0.8–2.0(m, 6H), 2.3–2.5(m, 3H), 3.68(s, 3H), 4.25(s, 2H)

REFERENCE EXAMPLE 11

Preparation of 2-(5-oxo-3-pentynyl)cyclopropanecarboxylic acid methyl ester

Oxalyl chloride (0.40 g, 3.1 mmol) was dissolved in dichloromethane, and the solution was cooled to −40° C. A solution of dimethyl sulfoxide (0.52 g, 6.2 mmol) in dichloromethane (2 ml) was added thereto over a period of 5 minutes, and the mixture was stirred for 20 minutes. A solution of 2-(5-hydroxy-3-pentynyl)cyclopropanecarboxylic acid methyl ester (0.37 g, 2 mmol) in dichloromethane (5 ml) was added thereto, and the mixture was stirred for 30 minutes. Then, triethylamine (1.7 ml, 12 mmol) was added thereto. The temperature was raised to 0° C., and a saturated sodium chloride aqueous solution was added thereto. The product was extracted with dichloromethane, dried over anhydrous magnesium sulfate and then purified by silica gel column chromatography to obtain the above identified compound (0.35 g, yield: 96%).

REFERENCE EXAMPLE 12

Preparation of (1S*,3S*)-3-(3-(tetrahydropyranyloxy-1-propynyl)cyclopentanecarboxylic acid methyl ester To a solution of a borane-dimethylsulfide complex (1.98 ml, 20.2 mmol) in THF (18.3 ml), a 1M THF solution of 2,3-dimethyl-2-butene (20.2 ml, 20.2 mmol) was added at 0° C., and the mixture was stirred at the same temperature. Two hours later, the reaction solution was cooled to −25° C., and a solution of 3-cyclopentenecarboxylic acid methyl ester (2.55 g, 20.2 mmol) in THF (20 ml) was dropwise added thereto. The mixture was stirred at the same temperature for 1.5 hours. Then, methanol (1.64 ml) was dropwise added thereto. The reaction temperature was raised to 0° C., and the mixture was stirred for one hour. The reaction solution was concentrated under reduced pressure, dried and then dissolved in THF (20 ml). Separately, a n-butyllithium/1.5M hexane solution (1.37 ml, 20.6 mmol) was added at 0° C. to a solution of propargyl tetrahydropyranyl ether (2.83 g, 20.2 mmol) in THF (20 l), and the mixture was stirred for one hour. This solution was dropwise added at 0° C. to the above THF solution (10 ml). Then, the reaction solution was cooled to −78° C., and a solution of iodine (5.13 g, 20.2 mmol) in THF (10 ml) was dropwise added thereto, and the mixture was stirred at the same temperature for one hour and at room temperature for two hours. A 2N sodium hydroxide aqueous solution (12.1 ml) and a 30% hydrogen peroxide aqueous solution (2.83 ml) were dropwise added thereto, and the mixture was stirred for 5 minutes, then diluted with ethyl acetate (150 ml) and washed with a saturated sodium thiosulfate aqueous solution (150 ml) and a saturated sodium chloride aqueous solution (150 ml). The organic layer was dried over anhydrous magnesium sulfate and then concentrated under reduced pressure. The residue was purified by silica gel column chromatography to obtain the above identified compound (2.56 g, 47.6%).

$^1$N-NMR(CDCl$_3$) $\delta$1.50–2.10(m, 12H), 2.80–3.01(m, 2H), 3,48–3.60(m, 1H), 3.67(s, 3H), 3.80–3.92(m, 1H), 4.18(d, J=15 Hz, 1H), 4.30(d, J=15 Hz, 1H), 4.70–4.80(m, 1H)

REFERENCE EXAMPLE 13

Preparation of (1S*,3S*)-3-(3-hydroxy-1-propynyl)cyclopentanecarboxylic acid methyl ester The carboxylic acid methyl ester (1.0 g, 3.75 mol) prepared in Reference Example 12 was dissolved in methanol (4 ml), and pyridinium p-toluenesulfonate (PPTS (100 mg, 0.4 mmol)) was added thereto. The mixture was stirred at 50° C. for one hour and 30 minutes. The reaction solution was concentrated under reduced pressure and purified by silica gel column chromatography to obtain the above identified compound (532 mg, 78.0%).

$^1$N-NMR(CDCl$_3$) $\delta$1.60–2.10(m, 6H), 2.80–3.02(m, 2H), 3.68(s, 3H), 4.24(s, 2H)

REFERENCE EXAMPLE 14

Preparation of (1S*,3S*)-3-(3-oxo-1-propynyl)cyclopentanecarboxylic acid methyl ester Using the compound (1.95 g, 10.7 mmol) prepared in Reference Example 13, the above identified compound (1.31 g, yield: 67.7%) was prepared in the same manner as in Reference Example 6.

$^1$N-NMR(CDCl$_3$) $\delta$1.80–2.35(m, 6H), 2.95–3.10(m, 2H), 3.69(s, 3H), 9.19(s, 1H)

REFERENCE EXAMPLE 15

Preparation of (1S*,3R*)-3-(3-tetrahydropyranyloxy-1-propynyl)cyclopentanecarboxylic acid methyl ester To a solution of diisopropylamine (16.6 ml, 118.4 mmol) in THF (250 ml), a 1.5M hexane solution of N-butyllithium (71.0 ml, 1.6.6 mmol) was added at 0° C., and the mixture was stirred for 15 minutes. The reaction solution was cooled to −70° C., and then a solution of the compound (15.8 g, 59.2 mmol) prepared in Reference Example 12, in THF (960 ml), was dropwise added thereto. The mixture was stirred at the same temperature for 20 minutes. The reaction solution was poured into a saturated ammonium chloride aqueous solution (300 ml) and extracted with ethyl ether (150 ml×2). The organic layer was dried over anhydrous magnesium sulfate, and then the solvent was distilled off under reduced pressure. The residue was purified by silica gel column chromatography (hexane:ethyl acetate=20:1 to 4:1) to obtain the above identified compound (2.34 g, 8.76 mmol, yield: 14.8%) and recovered starting material (8.53 g, yield: 54.0%).

$^1$N-NMR(CDCl$_3$) $\delta$1.50–2.38(m, 12H), 2.60–2.84(m, 2H), 3,48, 3.60(m, 1H), 3.68(s, 3H), 3.80– 3.92(m, 1H), 4.19(d, J=15 Hz, 1H), 4.30(d, J=15 Hz, 1H), 4.75–4.85(m, 1H)

REFERENCE EXAMPLE 16

Preparation of (1S*,3R*)-3-(3-hydroxy-1-propynyl)cyclopentanecarboxylic acid ester Using the compound (2.34 g, 8.76 mmol) prepared in Reference Example 15, the above identified compound (1.41 g, 7.75 mmol, yield: 88.5%) was obtained in the same manner as in Reference Example 13.

$^1$N-NMR(CDCl$_3$) δ1.72–2.35(m, 6H), 2.62–2.90(m, 2H), 3.69(s, 3H), 4.25(s, 2H)

REFERENCE EXAMPLE 17

Preparation of (1S*,3R*)-3-(3-oxo-1-propynyl)cyclopentanecarboxylic acid methyl ester Using the compound (1.40 g, 7.75 mmol) prepared in Reference Example 16, the above identified compound (1.08 g, 6.05 mmol, yield: 77.4%) was obtained in the same manner as in Reference Example 6.

$^1$N-NMR(CDCl$_3$) δ1.80–2.42(m, 6H), 2.75–2.95(m, 2H), 3.70(s, 3H), 9.19(s, 1H)

REFERENCE EXAMPLE 18

Preparation of 4-(t-butyldimethylsiloxymethyl)-1-cyclohexanecarboaldehyde 1,4-cyclohexanedimethanol (72.1 g) was dissolved in N,N-dimethylformamide (500 ml), and imidazole (68.1 g) and t-butyldimethylsilyl chloride (65.4 g) were added thereto. The mixture was stirred at room temperature for 14 hours. It was poured into a saturated sodium bicarbonate aqueous solution, then extracted with ethyl ether and dried. It was purified by silica gel column chromatography to obtain a monosilyl ether (72.5 g).

Then, a solution of dimethylsulfoxide (30.1 ml) in methylene chloride (95 ml) was added at −78° C. to a solution of oxalyl chloride (18.5 ml) in methylene chloride (480 ml). The mixture was stirred for 5 minutes, and then above-mentioned solution of the monosilyl ether (50 g) in methylene chloride (190 ml) was added thereto at −78° C. The mixture was stirred for further 30 minutes. Triethylamine (135 ml) was dropwise added thereto at −78° C., then the temperature was gradually raised to room temperature. The reaction mixture was poured into water (1 l), and the aqueous layer was extracted with methylene chloride. The extract solutions were put together and washed with an aqueous sodium chloride solution, then dried, concentrated and thereafter purified by column chromatography to obtain the above identified compound (49 g).

$^1$N-NMR(CDCl$_3$) δ0.84–0.85(m, 9H), 3.37(m, 2H), 9.58(s, 1H)

REFERENCE EXAMPLE 19

Preparation of 4-(2,2-dibromovinyl)-1-cyclohexanemethanol t-butyldimethylsilyl ether To a solution of the above-mentioned aldehyde (57.6 g) in methylene chloride (600 ml), solution of triphenylphosphine (118 g) and carbon tetrabromide (81.9 g) in methylene chloride (200 ml) was added at 0° C. The mixture was stirred for one hour and then poured into a saturated sodium bicarbonate aqueous solution. The product was extracted with ethyl ether. The extract solution was washed with an aqueous sodium chloride solution, then dried and purified by column chromatography to obtain the above identified compound (67.6 g).

$^1$N-NMR(CDCl$_3$) δ0.86(s, 9H), 3.4(m, 2H)

REFERENCE EXAMPLE 20

Preparation of 4-(-3-tetrahydropyranyloxy-1-propynyl)cyclohexanemethanol t-butyldimethylsilyl ether To a solution of the above dibromide (62 g) in tetrahydrofuran (500 ml), n-butyllithium (a 1.5M hexane solution, 207 ml) was added, and the mixture was cooled to −78° C. Then, paraformamide (9.34 g) was added thereto, and the mixture stirred at −20° C. for 12 hours and at room temperature for 2 hours. Then, the mixture was poured into a saturated sodium bicarbonate aqueous solution and extracted with ethyl ether. The extract solution was washed with an aqueous sodium chloride solution, then dried and concentrated. The residue was dissolved in methylene chloride (310 ml), and 2,3-dihydropyrane (15.7 ml) and p-toluenesulfonic acid (2.97 g) were added thereto. The mixture was stirred at room temperature for 14 hours. It was then poured into a saturated sodium bicarbonate aqueous solution, then extracted with methylene chloride, dried and concentrated. Then, it was purified by column chromatography to obtain the above identified compound (31.6 g).

$^1$N-NMR(CDCl$_3$) δ0.86(s, 9H), 3.37(m, 2H), 4,79(m, 1H)

REFERENCE EXAMPLE 21

Preparation of 4-(3-tetrahydropyranyloxy-1-propynyl)-1-cyclohexanemethanol

To a solution of the above silyl ether (31.6 g) in tetrahydrofuran (170 ml), tetrabutyl ammonium fluoride (1M, a tetrahydrofuran solution, 94.8 ml) was added at 0° C., and the mixture was stirred at room temperature for 14 hours, then concentrated and purified by column chromatography to obtain the above identified compound (21.3 g).

$^1$N-NMR(CDCl$_3$) δ4.18(m, 1H)

REFERENCE EXAMPLE 22

Preparation of 4-(3-tetrahydropyranyloxy-1-propynyl)-1-cyclohexanecarbaldehyde

To a solution of oxalyl chloride (6.38 ml) in methylene chloride (165 ml), a solution of dimethylsulfoxide (10.38 ml) in methylene chloride (35 ml) was dropwise added at −78° C. The mixture was stirred for 10 minutes, and then a solution of the above alcohol (16.78 g) in methylene chloride (655 ml) was dropwise added thereto at −78° C., and the mixture was stirred for 30 minutes. Triethylamine (46.3 ml) was dropwise added thereto at −78° C., and the temperature was gradually raised to room temperature. The mixture was stirred at room temperature for 30 minutes and then poured into water and extracted with methylene chloride. The extract solution was washed with an aqueous sodium chloride solution, then dried, concentrated and purified by column chromatography to obtain the above identified compound (16.0 g).

$^1$N-NMR(CDCl$_3$) δ4.80(m, 1H), 9.63(m, 1H)

REFERENCE EXAMPLE 23

Preparation of 4-(3-hydroxy-1-propynyl)-1-cyclohexanecarboxylic acid methyl ester The above aldehyde (16.0 g) was added at 0° C. to a mixture comprising an aqueous solution (45 ml) of silver nitrate (22.7 g) and an aqueous solution (45 ml) of sodium hydroxide, and the mixture was stirred at 0° C. for 15 minutes. The reaction mixture was filtered through Celite, washed with hot water and then left to cool. The reaction mixture was acidified with hydrochloric acid and then extracted with ethyl ether. The extract solution was dried and concentrated. The residue was dissolved in ethyl ether (120 ml), and diazomethane (0.5M, an ethyl ether solution, 13 ml) was dropwise added thereto at 0° C. The reaction solution was concentrated, and the residue was dissolved in ethanol (100 ml). Pyridinium p-toluenesulfonate (0.89 g) was added thereto, and the mixture was stirred at 40° C. for 30 minutes and at 55° C. for 3.5 hours. The mixture was poured into a saturated sodium bicarbonate aqueous solution, then extracted with chloroform, dried and concentrated. Then, it was purified by column chromatography to obtain the above identified compound (7.42 g).

$^1$N-NMR(CDCl$_3$) δ1.3–2.4(m, 10H), 3.67(m, 3H), 4.25(m, 2H) IR(CDCl$_3$) 3600, 3460, 2210, 1720 cm$^{-1}$

REFERENCE EXAMPLE 24

Preparation of 4-(3-oxo-1-propynyl)cyclohexanecarboxylic acid methyl ester

A solution of dimethylsulfoxide (5.91 ml) in methylene chloride (19 ml) was added at −78° C. to a solution of oxalyl chloride (3.63 ml) in methylene chloride (95 ml), and the mixture was stirred for 5 minutes. Then, a solution of an alcohol (7.02 g) in methylene chloride (38 ml) was dropwise added thereto at −78° C., and the mixture was stirred for 30 minutes. Then, triethylamine (26.4 ml) was added at −78° C., and the temperature was raised to room temperature. Then, the mixture was stirred for 30 minutes. Then, it was poured into water and extracted with methylene chloride. The extract solution was washed with an aqueous sodium chloride solution, dried and concentrated. Then, it was purified by column chromatography to obtain the above identified methyl ester (5.2 g).

$^1$N-NMR(CDCl$_3$) δ1.4–2.5(m, 10H), 3.68(m, 3H), 9.19(m, 1H)

EXAMPLE 1

Sodium salt of 2,3-methylene-7α-fluoro-17,20-dimethylPGI$_2$

Example 1-1

Preparation of 5,6-dehydro-2,3-methylene-7-hydroxy-17,20-dimethylPGE$_2$ methyl ester 11,15-bis(t-butyldimethyl)silyl ether t-Butyllithium (factor=1.5, a pentane solution, 2.7 ml, 4.0 mmol) was added to ethyl ether (5 ml) at −78° C. (1E,3S,5S)-3-t-butyldimethylsiloxy-5-methyl-1-iodo-1-nonene (0.79 g, 2.0 mmol) was dissolved in ethyl ether (5 ml) and dropwise added thereto over a period of 10 minutes. The mixture was stirred for 2 hours at −78° C. Then, pentyl copper (0.26 g, 2.0 mmol) and HMPT (0.65 g, 4.0 mmol) were dissolved in ethyl ether (10 ml) and dropwise added thereto over a period of 15 minutes. One hour and thirty minutes later, (4R)-4-t-butyldimethylsiloxy-2-cyclopentenone (0.40 g, 1.9 mmol) was dissolved in ethyl ether (10 ml) and added thereto. Twenty minutes later, the temperature was raised to −40° C. Further, 2-(4-oxo-2-butynyl)cyclopropanecarboxylic acid methyl ether (0.32 g, 2.0 mmol) was dissolved in ethyl ether (10 ml) and dropwise added thereto over a period of 15 minutes. The mixture was stirred for one hour at −40° C., and then a saturated ammonium chloride aqueous solution was added thereto, and the product was extracted with ethyl ether. The extract was purified by silica gel chromatography to obtain the above identified compound (0.66 g, yield: 53%).

$^1$N-NMR(CDCl$_3$) δ–0.1–0.1(m, 12H), 0.6–1.0(m, 27H), 1.0–1.5(m, 9H), 2.2–2.9(m, 9H), 3.65(s, 3H), 4.0–4.2(m, 2H), 5.5–5.7(m, 2H)

Example 1-2

Preparation of 5,6-dehydro-2,3-methylene-7-trimethylsiloxy-17,20-dimethylPGF$_2$α methyl ester 11,15-bis(t-butyldimethyl)silyl-9-triethylsilyl ether The alcohol (0.40 g, 0.62 mmol) prepared in Example 1-1 was dissolved in dichloromethane (5 ml), and the solution was cooled to 0° C. Pyridine (0.50 ml, 6.2 mmol) and chlorotrimethylsilane (0.20 ml, 1.55 mmol) were added thereto, and post-treatment was conducted. The crude product was dissolved in methanol (6 ml), and the solution was cooled to −30° C. Then, sodium borohydride (78 mg, 2.1 mmol) was added thereto, and the mixture was stirred for 40 minutes. A saturated ammonium chloride aqueous solution was added thereto, and post-treatment was conducted.

The crude product thereby obtained was dissolved in pyridine (5 ml), and the solution was cooled to −12° C. Chlorotriethylsilane (0.22 ml, 1.3 mmol) was added thereto, and the mixture was stirred at 0° C. for 30 minutes. A saturated sodium hydrogen carbonate aqueous solution was added thereto, and the product was extracted with hexane, dried and concentrated. Then, it was purified by silica gel column chromatography to obtain the above identified compound (0.32 g).

$^1$N-NMR(CDCl$_3$) δ–0.1–0.1(m, 12H), 0.5–0.7(m, 6H), 0.7–1.0(m, 36H), 1.1–1.6(m, 9H), 1.9–2.7(m, 7H), 3.63(s, 3H), 3.8–4.2(m, 3H), 4.5–4.7(m, 1H), 5.4–5.6(m, 2H)

Example 1-3

Preparation of 5,6-dehydro-2,3-methylene-7β-fluoro-17,20-dimethylPGF$_2$α methyl ester 11,15-bis(t-butyldimethyl)silyl-9-triethylsilyl ether The trimethylsilyl ether (0.32 g, 0.39 mmol) prepared in Example 1-2 was dissolved in 1,1,2-trichloro-1,2,2-trifluoroethane (8 ml), and the solution was cooled to 0° C. Piperidinosulfur trifluoride (0.062 ml, 0.47 mmol) was added thereto, and the mixture was stirred at room temperature for 5.5 hours. Then, triethylamine was added thereto, and a saturated potassium carbonate aqueous solution was added thereto. The product was purified by silica gel column chromatography to obtain the above identified compound (0.21 g).

$^1$N-NMR(CDCl$_3$) δ–0.1–0.1(m, 12H), 0.5–0.7(m, 6H), 0.7–1.0(m, 36H), 1.1–1.6(m, 9H), 1.9–2.7(m, 7H), 3.63(s, 3H), 3.85(l, J=6.5 Hz, 1H), 4.1–4.2(m, 1H), 4.2–4.3(m,

1H), 5.35(dd, J=48, 7.5 Hz, 1H), 5.4–5.5(m, 2H) $^{19}$F-NMR(CDCl$_3$, CCl$_3$F standard) −170.0 ppm m

Example 1-4

Preparation of 5,6-dehydro-2,3-methylene-7β-fluoro-17,20-dimethylPFG$_2$α methyl ester 11,15-bis(t-butyldimethyl)silyl ether The triethylsilyl ether (0.21 g, 0.27 mmol) prepared in Example 1-3 was dissolved in ethanol (5 ml), and pyridinium p-toluene sulfonate (7 mg, 0.027 mmol) was added at 0° C. The mixture was stirred at room temperature for 3 hours. A saturated sodium hydrogen carbonate aqueous solution was added thereto, and the product was extracted with dichloroemthane. The extract was dried, concentrated and the purified by silica gel column chromgatography to obtain the above identified compound (95 mg).

$^1$N-NMR(CDCl$_3$) δ−0.1–0.1(m, 12H), 0.8–1.0(m, 36H), 1.0–2.0(m, 13H), 2.4–2.6(m, 2H), 3.12(dd, J=8.4, 11.2 Hz, 1H), 3.62(s, 3H), 4.0–4.2(m, 2H), 4.2–4.4(m, 1H), 5.2–5.5(m, 3H) $^{19}$F-NMR(CDCl$_3$, CCl$_3$F standard) −169.3(dm, J=47.1 Hz)

Example 1-5

Preparation of 2,3-methylene-7β-fluoro-17,20-dimethylPGF$_2$α methyl ester 11,15-bis(t-butyldimethyl)silyl ether The compound (95 mg, 0.15 mmol) prepared in Example 1-4 was dissolved in benzene (2.5 ml) and cyclohexane (2.5 ml), and cyclohexene (0.15 ml, 1.0 mmol) and a Lindlar catalyst (20 mg) were added thereto, followed by hydrogenation at 0° C. for 1.5 hours.

$^1$NMR(CDCl$_3$) δ0.0–0.1(m, 12H), 0.6–1.0(m, 27H), 1.0–2.4(m, 16H), 3.70(s, 3H), 4.0–4.2(m, 2H), 4.3–4.4(m, 1H) 5.2–5.7(m, 5H) $^{19}$F-NMR(CDCl$_3$, CCl$_3$F standard) −167.0 ppm (d, J=48 Hz)

Example 1-6

Preparation of 2,3-methylene-7α-fluoro-17,20-dimethylPGI$_2$ methyl ester 11,15-bis(t-butyldimethyl)silyl ether The olefin (100 mg, 0.15 mmol) prepared in Example 1-5 was dissolved in acetonitrile (4 ml), and N-iodosuccinic imide (0.49 g, 2.2 mmol) was added, and the mixture was stirred at 40° C. for 24 hours. Then, 10% sodium thiosulfate was added, and the product was extracted with dichloromethane. The organic layer was dried, concentrated and purified by silica gel chromatography to obtain a cyclized product (83 mg).

The above cyclized product (83 mg) was dissolved in toluene (5 ml), and 1,8-diazobicyclo[5.4.0]-7-undecene (0.15 ml) was added thereto. The mixture was stirred at 110° C. for 18 hours. A saturated sodium chloride aqueous solution was added thereto, and the product was extracted with ethyl ether. The organic layer was dried, concentrated and then purified by silica gel column chromatography to obtain the above identified compound (14 mg).

$^1$N-NMR(CDCl$_3$) δ−0.1–0.1(m, 12H), 0.7–1.0(m, 27H), 1.0– 1.8(m, 12H), 2.0–2.2(m, 1H, H-4), 2.3–2.4(m, 1H, H-10), 2.4–2.6(m, 1H, H-8, 2.7–2.8(m, 1H, H-12), 3.62(,s, 3H), 3.8–3.9(m, 1H, H-11), 4.1–4.2(m, 1H, H-15), 4.5–4.6(m, 2H, H-5, H-9), 5,32(dd, J=53, 7.5 Hz, 1H), 5.4–5.6(m, 2H) $^{19}$F-NMR(CDCl$_3$, CCl$_3$F standard) −184.0 ppm (d, J=53 Hz, 0.5F), 184.2 ppm (d, J=51.7 Hz, 0.5F)

Example 1-7

Preparation of 2,3-methylene-7α-fluoro-17,20-dimethyl PGI$_2$ methyl ester

The t-butyldimethylsilyl ether product (13 mg) prepared in Example 1-6 was dissolved in tetrahydrofuran (1 ml), and tetrabutyl ammonium fluoride (factor=1, a tetrahydrofuran solution, 0.16 ml, 0.16 mmol) was added thereto at 0° C. The mixture was stirred at room temperature for 3 hours. Then, a saturated ammonium sulfate solution was added thereto, and the product was extracted with ethyl acetate. The organic layer was dried, concentrated and purified by a florisil column to obtain the above identified compound (9 mg).

$^1$N-NMR(CDCl$_3$) δ0.7–1.0(m, 9H), 1.0–1.9(m, 11H), 2.4–2.8(m, 5H), 3.60(s, 3H), 3.85(l, J=7.5 Hz, 1H), 4.10(l, J=6.5 Hz, 1H), 4.5–4.6(m, 2H), 5.35(dm, 1H), 5.5–5.69(m, 2H) $^{19}$F-NMR(CDCl$_3$, CCl$_3$F standard) −186.0 ppm (d, J=55.0 Hz, 0.5F), −188.0 ppm (d, J=55.5 Hz, 0.5F)

Example 1-8

Preparation of sodium salt of 2,3-methylene-7α-fluoro-17,20-dimethylPGI$_2$

The methyl ester (9 mg) prepared in Example 1-7 was dissolved in ethanol (0.30 ml), and 0.1N sodium hydroxide (0.28 ml) was added thereto. The mixture was stirred at 25° C. for 36 hours. The product was concentrated and dried to obtain the above identified compound.

EXAMPLE 2

Sodium salt of 4-homo-2,3-methylene-7α-fluoro-17,20,-dimethylPGI$_2$

Example 2-1

Preparation of 5,6-dehydro-4-homo-2,3-methylene-7-hydroxy-17,20-dimethylPGE$_2$ methyl ester 11,15-bis(t-butyldimethyl)silyl ether t-Butyllithium (factor=1.5, a pentane solution, 2.7 ml, 4.0 mmol) was added to ethyl ether (5 ml) at −78° C. (1E,3S,5S)-3-t-butyldimethylsiloxy-5-methyl-1-iodo-1-nonene (0.79 g, 2.0 mmol) was dissolved in ethyl ether (5 ml) and dropwise added thereto over a period of 10 minutes. The mixture was stirred for two hours at −78° C. Then, pentyne copper (0.26 g, 2.0 mmol) and HMPT (0.65 g, 4.0 mmol) were dissolved in ethyl ether (10 ml) and dropwise added thereto over a period of 15 minutes. One hour and thirty minutes later, (4R)-4-t-butyldimethylsiloxy-2-cyclopentenone (0.40 g, 1.9 mmol) was dissolved in ethyl ether (10 ml) and added thereto. Twenty minutes later, the temperature was raised to −40° C. Further, 2-(5-oxo-3-pentynyl)cyclopropane carboxylic acid methyl ester (0.35 g, 2.0 mmol) was dissolved in ethyl ether (10 ml) and dropwise added thereto over a period of 15 minutes. The mixture was stirred for one hour at −40° C. Then, a saturated ammonium chloride aqueous solution was added thereto, and the product was extracted with ethyl ether. It was then purified by silica gel column chromatography to obtain the above identified compound (0.66 g, yield: 53%).

$^1$N-NMR(CDCl$_3$) δ–0.1–0.1(m, 12H), 0.6–1.0(m, 27H), 1.0–1.5(m, 11H), 2.1–2.4(m, 7H), 2.6–2.8(m, 2H), 3.62(s, 3H), 4.0–4.2(m, 2H), 5.5–5.6(m, 2H)

Example 2-2

Preparation of
5,6-dehydro-4-homo-2,3-methylene-7-trimethylsiloxy-17,20-dimethylPGF$_2α$ methyl ester 11,15-bis(t-butyldimethyl)silyl ether Using the alcohol (0.66 g, 1.0 mmol) prepared in Example 2-1, the above identified compound (0.59 g) was obtained in the same manner as in Example 1-2.

Example 2-3

Preparation of
5,6-dehydro-4-homo-2,3-methylene-7α-fluoro-17,20-dimethylPGF$_2α$ methyl ester 11,15-bis(t-butyldimethyl)silyl-9-triethylsilyl ether Using the trimethylsilyl ether (0.59 g, 0.70 mmol) prepared in Example 2-2, fluorination was conducted in the same manner as in Example 1-3 to obtain the above identified compound (0.39 g).

$^1$N-NMR(CDCl$_3$) δ–0.1–0.1(m, 12H), 0.5–0.6(m, 6H), 0.7–1.0(m, 36H), 1.1–1.6(m, 11H), 1.8–2.4(m, 6H), 2.6–2.7(m, 1H), 3.63(s, 3H), 3.86(l, J=6.5 Hz, 1H), 4.1–4.2(m, 1H), 4.2–4.3(m, 1H), 5.32(dd, J=49, 7.5 Hz, 1H), 5.4–5.6(m, 2H) $^{19}$F-NMR(CDCl$_3$, CCl$_3$F standard) –169.6 ppm(m)

Example 2-4

Preparation of
5,6-dehydro-4-homo-2,3-methylene-7β-fluoro-17,20-dimethylPGF$_2α$ methyl ester 11,15-bis(t-butyldimethyl)silyl ether Using the triethylsilyl ether (0.39 g, 0.50 mmol) prepared in Example 2-3, the above identified compound (2.04 g) was prepared in the same manner as in Example 1-4.

Example 2-5

Preparation of
4-homo-2,3-methylene-7β-fluoro-17,20-dimethylPGF$_2α$ methyl ester 11,15-bis(t-butyldimethyl)silyl ether Using the acetylene (0.24 g) prepared in Example 2-4, the above identified compound (0.21 g) was obtained in the same manner as in Example 1-5.

$^1$N-NMR(CDCl$_3$) δ0.0–0.1(m, 12H), 0.6–1.0(m, 27H), 1.0–2.4(m, 18H), 3.65(s, 3H), 4.0–4.2(m, 2H), 4.3–4.4(m, 1H), 5.2–5.7(m, 5H) $^{19}$F-NMR(CDCl$_3$, CCl$_3$F standard) –167.2 ppm (d, J=56 Hz)

Example 2-6

Preparation of
4-homo-2,3-methylene-7α-fluoro-17,20-dimethyl-PGF$_2$ methyl ester 11,15-bis(t-butyldimethyl)silyl ether Using the olefin (0.21 g, 0.35 mmol) prepared in Example 2-5, the above identified compound (34 mg) was prepared in the same manner as in Example 1-6.

$^1$N-NMR(CDCl$_3$) δ–0.1–0.1(m, 12H), 0.6–1.0(m, 27H), 1.0–1.8(m, 13H), 2.0–2.2 (m, 2H), 2.3–2.4(m, 1H), 2.4–2.6(s, 1H), 2.7–2.8(m, 1H), 3.62(s, 3H), 3.80(l, J=7.5 Hz, 7.5 Hz, 1H), 4.1–4.2(m, 1H), 4.5—4.5(m, 2H), 5.28(dd, J=56, 7.5 Hz, 1H), 5.4–5.6(m, 2H) $^{19}$F-NMR(CDCl$_3$, CCl$_3$F standard) –182.6 ppm (d, J=56 Hz)

Example 2-7

Preparation of
4-homo-2,3-methylene-7α-fluoro-17,20-dimethylPGI$_2$ methyl ester Using the silyl ether product (34 mg) prepared in Example 2-6, the above identified compound (24 mg) was prepared in the same manner as in Example 1-7.

$^1$N-NMR(CDCl$_3$) δ0.7–1.0(m, 6H), 0.87(d, J=6.3 Hz, 3H), 1.0–1.9(m, 13H), 2.4–3.0(m, 5H), 3.66(s, 1.5H), 3.67(s, 1.5H), 3.8–3.9(m, 1H), 4.1–4.2(m, 1H), 4.5–4.7(m, 1H), 5.40(d, J= 55Hz, 1H), 5.56(d, J=4.1 Hz, 1H) $^{19}$F-NMR(CDCl$_3$, CCl$_3$F standard) –187.0 ppm (d, J=57.0 Hz, 0.5F), –187.3 ppm(d, J=54.7 Hz), 0.5F)

Example 2-8

Preparation of sodium salt of
4-homo-2,3-methylene-7α-fluoro-17,20-dimethylPGI$_2$ The methyl ester (24 mg, 0.06 mmol) prepared in Example 2-7, was dissolved in ethanol (0.73 ml), and 0.1N sodium hydroxide (0.68 ml) was added thereto. The mixture was stirred at 25° C. for 48 hours. Then, it was concentrated and dried to obtain the above identified compound.

EXAMPLE 3

(1S*,3S*)-2,3-ethylene-7α-fluoro-17,20-dimethylPGI$_2$ methyl ester and sodium salt

Example 3-1

Preparation of
(1S*,3S*)-2,4-ethylene-5,6-dehydro-7-hydroxy-17,20-dimethyl-PGI$_2$-methyl ester 11,15-bis(t-butyldimethyl)silyl ether Using the aldehyde (1.36 g, 7.56 mmol) prepared in Reference Example 14, the above identified compound (3.07 g, yield: 67.2%) was prepared in the same manner as in Example 1-1.

$^1$N-NMR(CDCl$_3$) δ0.00–0.20(m, 12H), 0.80–1.00(m, 24H), 3.69(s, 3H), 4.15–4.25(m, 2H), 5.54–5.70(m, 2H)

Example 3-2

Preparation of
(1S*,3S*)-2,4-ethylene-5,6-dehydro-7-trimethylsiloxy-17,20-dimethylPGF$_2α$ methyl ester 11,15-bis(t-butyldimethyl)silyl ether Using the compound (3.07 g, 4.62 mmol) prepared in Example 3-1, the above identified compound (2.77 g, yield: 70.5%) was prepared in the same manner as in Example 1-2.

$^1$N-NMR(CDCl$_3$) δ0.00–0.20(m, 21H), 0.50–0.70(m, 6H), 0.80–1.00(m, 30H), 3.68(s, 3H), 4.15–4.25(m, 2H), 5.50–5.70(m, 2H)

Example 3-3

Preparation of
(1S*,3S*)-2,4-ethylene-5,6-dehydro-7β-fluoro-17,20-dimethylPGF$_2α$ methyl ester 11,15-bis(t-butyldimethyl)silyl-9-triethylsilyl ether Using the compound (2.77 g, 3.26 mmol) prepared in Example 3-2, the above identified compound (2.15 g, yield: 84.9% was prepared in the same manner as in Example 1-3.

$^1$N-NMR(CDCl$_3$) δ0.00–0.20(m, 12H), 0.50–0.70(m, 6H), 0.80–1.00(m, 30H), 3.68(s, 3H), 4.15–4.25(m, 2H), 5.40–5.70(m, 3H) $^{19}$F-NMR(CDCl$_3$CCl$_3$F standard) −169.0 ppm(m)

Example 3-4

Preparation of
(1S*,3S*)-2,4-ethylene-5,6-dehydro-7β-fluoro-17,20-dimethylPGF$_{2α}$ methyl ester 11,15-bis(t-butyldimethyl)silyl ether Using the compound (2.15 g, 2.77 mmol) prepared in Example 3-3, the above identified compound (1.13 g, mmol, yield: 61.5%) was prepared in the same manner as in Example 1-4.

$^1$N-NMR(CDCl$_3$) δ0.00–0.20(m, 12H), 0.80–1.00(m, 24H), 3.68(s, 3H), 4.08–4.24(m, 2H), 5.28–5.56(m, 3H) $^{19}$F-NMR(CDCl$_3$, CCl$_3$F standard) −169.0 ppm(m)

Example 3-5

Preparation of
(1S*,3S*)-2,4-ethylene-7α-fluoro-17,20-dimethyl-PGI$_2$ methyl ester 11,15-bis(t-butyldimethyl)silyl ether Using the compound (1.13 g, 1.70 mmol) prepared in Example 3-4, the above identified compound was prepared in the same manner as in Example 1-5 and Example 1-6. Low polarity isomer (127 mg, yield: 11.2%), and the high polarity isomer (67 mg, yield: 5.9%).

Low polarity isomer: $^1$N-NMR(CDCl$_3$) δ0.00–0.10(m, 12H), 0.80–0.90(m, 24H), 3.63(s, 3H), 5.26(dd, J=56 Hz, J=9 Hz, 1H), 5.50–5.55(m, 2H) $^{19}$F-NMR(CDCl$_3$, CCl$_3$F standard) −183.4 ppm(dd, J=56 Hz, 9 Hz)

High polarity isomer: $^1$N-NMR(CDCl$_3$) δ0.02(s, 12H), 0.84–0.88(m, 24H), 3.65(s, 3H), 5.26(dd, J=56 Hz, J=9 Hz), 5.50–5.55(m, 2H) $^{19}$F-NMR(CDCl$_3$, CCl$_3$F standard) −183.4 ppm(dd, J=56 Hz, 9 Hz)

Example 3-6

Preparation of
(1S*,3S*)-2,4-ethylene-7α-fluoro-17,20-dimethylPGI$_2$-methyl ester Using the compounds prepared in Example 3-5 i.e. the low polarity isomer (127 mg, 0.19 mmol) and the high polarity isomer (67 mg, 0.10 mmol), the above identified compounds were obtained in the same manner as in Example 1-7. The low polarity isomer (58 mg, yield: 70.2%), and the high polarity isomer (33 mg, yield: 75.1%).

Low polarity isomer: $^1$N-NMR(CDCl$_3$) δ0.80–0.95(m, 6H), 3.67(s, 3H), 3.80–3.95(m, 4.10–4.20(m, 1H), 4.55–4.65(m, 2H), 5.35(dd, J=56 Hz, 9 Hz, 1H), 5.50–5.60(m, 2H) $^{19}$F-NMR(CDCl$_3$, CCl$_3$F standard) −185.6 ppm(dd, J=56 Hz, 9 Hz)

High polarity isomer: $^1$N-NMR(CDCl$_3$) δ0.80–0.95(m, 6H), 6.67(s, 3H), 3.80–3.95(m, 1H0, 4.10–4.20(m, 1H), 4.50–5.65(m, 1H), 4.10–4.20(m, 1H), 4.50–4.65(m, 2H), 5.35(dd, J=56 Hz, 9 Hz), 5.55–5.60(m, 2H) $^{19}$F-NMR(CDCl$_3$, CCl$_3$F standard) −184.9 ppm(dd, J=56 Hz, 9 Hz)

Example 3-7

Preparation of sodium salt of
(1S*,3S*)-2,4-ethylene-7α-fluoro-17,20-dimethyl-PGI$_2$ Using the low polarity isomer (96 mg) among the compounds prepared in Example 3-6, the low polarity isomer (38 mg) of the above identified compound was prepared in the same manner as in Example 1-8. Further, using the high polarity isomer (87 mg) among the compounds prepared in Example 3-6, the high polarity isomer (69 mg) of the above identified compound was prepared in the same manner as in Example 1-8.

Low polarity isomer: $^1$N-NMR(CDCl$_3$) δ0.92–1.05(m, 6H), 3.90–4.00(m, 1H), 4.12–4.25(m, 1H), 4.58–4.72(m, 2H) 5.45(dd, J=64 Hz, 8.4 Hz, 1H), 5.56–5.80(m, 2H) $^{19}$F-NMR(CDCl$_3$, CCl$_3$F standard) −186.0 ppm(d, 64 Hz)

High polarity isomer: $^1$N-NMR(CDCl$_3$) δ0.90–1.05(m, 6H), 3.88–4.02(m, 1H), 4.14(4.24(m, 1H), 4.58–4.70(m, 2H), 5.45(dd, J=64 Hz, 8.4 Hz, 1H), 5.55–5.80(m, 2H) $^{19}$F-NMR(CDCl$_3$, CCl$_3$F standard) −185.4 ppm(d, 64 Hz)

EXAMPLE 4

(1S*,3R*)-2,4-ethylene-7α-fluoro-17,20-dimethylPGI$_2$ methyl ester

Example 4-1

Preparation of
(1S*,3R*)-2,4-ethylene-5,6-dehydro-7-hydroxy-17,20-dimethylPGE$_2$ methyl ester-11,15-bis(t-butyldimethyl)silyl ether Using the aldehyde (1.09 g, 6.05 mmol) prepared in Reference Example 17, the above identified compound (2.28 g, yield: 62.2%) was prepared in the same manner as in Example 1-1

$^1$N-NMR(CDCl$_3$) δ0.00–0.20(m, 12H), 0.80–1.00(m, 24H), 3.67(s, 3H), 4.16–4.30(m, 2H), 5.50–5.70(m, 2H)

Example 4-2

Preparation of
(1S*,3R*)-2,4-ethylene-5,6-dehydro-7-trimethylsiloxy-17,20-dimethylPGF$_{2α}$ methyl ester-11,15-bis(t-butyldimethyl)silyl ether Using the compound (2.28 g, 3.42 mmol) prepared in Example 4-1, the above identified compound (1.98 g, yield: 68.1%) was prepared in the same manner as in Example 1-2.

$^1$N-NMR(CDCl$_3$) δ0.00–0.10(m, 21H), 0.50–0.65(m, 6H), 0.28–1.00(m, 30H), 3.67(s, 3H), 5.40–5.60(m, 2H)

Example 4-3

Preparation of
(1S*,3R*)-2,4-ethylene-5,6-dehydro-7β-fluoro-17,20-dimethylPGF$_{2α}$ methyl ester-11,15-bis(t-butyldimethyl)silyl-9-triethylsilyl ether Using the compound (1.98 g, 2.33 mmol) prepared in Example 4-2, the above identified compound (1.55 g, yield: 85.4%) was prepared in the same manner as in Example 1-3.

$^1$N-NMR(CDCl$_3$) δ0.00–0.10(m, 12H), 0.50–0.70(m, 6H), 0.80–1.00(m, 30H), 3.68(s, 3H), 5.20–5.60(m, 3H) $^{19}$F-NMR(CDCl$_3$, CCl$_3$F standard) −169.8 ppm (m)

Example 4-4

Preparation of
(1S*,3R*)-2,4-ethylene-5,6-dehydro-7β-fluoro-17,20-dimethylPGF$_{2α}$ methyl ester-11,15-bis(t-butyldimethyl)silyl ether Using the compound (1.55 g, 1.99 mmol) prepared in Example 4-3, the above identified compound (845 mg, yield: 64.0%) was prepared in the same manner as in Example 1-4.

$^1$N-NMR(CDCl$_3$) δ0.00–0.15(m, 12H), 0.85–0.95(m, 24H), 3.68(s, 3H), 4.10–4.20(m, 2H), 5.30–5.55(m, 3H)

$^{19}$F-NMR(CDCl$_3$, CCl$_3$F standard) −169.0 ppm (dd, J=56 Hz, 9 Hz)

Example 4-5

Preparation of (1S*,3R*)-2,4-ethylene-7α-fluoro-17,20-dimethyl-PGI$_2$α methyl ester-11,15-bis(t-butyldimethyl)silyl ether Using the compound (845 mg, 1.27 mmol) prepared in Example 4-4, the above identified compound (205 mg, yield: 24.3%) was prepared in the same manner as in Example 1-5 followed by Example 1-6.

$^1$N-NMR(CDCl$_3$) δ0.00–0.20(m, 12H), 0.80–0.95(m, 24H), 3.67(s, 3H), 5.30(dd, J=56 Hz, 1H), 5.55–5.60(m, 2H) $^{19}$F-NMR(CDCl$_3$, CCl$_3$F standard) −182.4 ppm(dd, J=56 Hz, 9 Hz), −182.8 ppm(dd, J=56 Hz, 9 Hz)

Example 4-6

Preparation of (1S*,3R*)-2,4-ethylene-7α-fluoro-17,20-dimethyl-PGI$_2$ methyl ester Using the compound (205 mg, 0.31 mmol) prepared in Example 4-5, the above identified compound (118 mg, yield: 87.5%) was prepared in the same manner as in Example 1-7.

$^1$N-NMR(CDCl$_3$) δ0.85–1.00(m, 6H), 3.67(s, 3H), 3.85–3.95(m, 1H), 4.15–4.25(m, 1H), 4.55–4.65(m, 1H), 5.38(dd, J=56 Hz, 9 Hz, 1H), 5.55–5.65(m, 2H) $^{19}$F-NMR(CDCl$_3$, CCl$_3$F standard) −184.5 ppm(dd, J=56 Hz, 9 Hz), −185.1 ppm(dd, J=56 Hz, 9 Hz)

EXAMPLE 5

2,4-ethylene-3α-homo-7α-fluoro-17,20-dimethylPGI$_2$ methyl ester

Example 5-1

Preparation of 2,4-ethylene-3α-homo-5,6-dehydro-7-hydroxy-17,20-dimethylPGE$_2$ methyl ester 11,15-bis(t-butyldimethyl)silyl ether Using the aldehyde (3.68 g, 19.9 mmol) prepared in Reference Example 24, the above identified compound (5.41 g, yield: 44%) was prepared in the same manner as in Example 1-1.

Example 5-2

Preparation of 2,4-ethylene-3α-homo-5,6-dehydro-7-trimethylsiloxy-17,20-dimethylPGF$_2$α methyl ester 11,15-bis(t-butyldimethyl)silyl ether Using the aldehyde (5.41 g, 7.99 mmol) prepared in Example 5-1, the above identified compound (4.39 g, yield: 64%) was prepared in the same manner as in Example 1-2.

$^1$N-NMR(CDCl$_3$) δ3.67(s, 3H), 5.4–5.7(m, 2H)

Example 5-3

Preparation of 2,4-ethylene-3α-homo-5,6-dehydro-7β-fluoro-17,20-dimethylPGF$_2$α methyl ester 11,15-bis(t-butyldimethyl)silyl-9-triethylsilyl ether Using the compound (4.39 g, 5.07 mmol) prepared in Example 5-2, the above identified compound (2.60 g, yield: 68%) was prepared in the same manner as in Example 1-3.

Example 5-4

Preparation of 2,4-ethylene-3α-homo-5,6-dehydro-7β-fluoro-17,20-dimethylPGF$_2$α methyl ester 11,15-bis(t-butyldimethyl)silyl ether Using the compound (2.60 g, 3.27 mmol) prepared in Example 5-3, the above identified compound (1.31 g, yield: 59%) was prepared in the same manner as in Example 1-4.

$^1$N-NMR(CDCl$_3$) δ3.67(m, 3H), 5.45(m, 2H) $^{19}$F-NMR(CDCl$_3$, CCl$_3$F standard) −168.4 ppm(m)

Example 5-5

Preparation of 2,4-ethylene-3α-homo-7α-fluoro-17,20-dimethylPGI$_2$ methyl ester 11,15-bis(t-butyldimethyl)silyl ether Using the compound (1.31 g, 1.92 mmol) prepared in Example 5-4, two types of isomers of the above identified compound i.e. a low polarity isomer (115 mg, yield: 8.8%) and a high polarity isomer (102 mg, yield: 7.8%) were prepared in the same manner as in Example 1-5, followed by Example 1-6.

Low polarity isomer: $^1$N-NMR(CDCl$_3$) δ3.67(s, 3H), 5.54(m, 1H) $^{19}$F-NMR(CDCl$_3$, CCl$_3$F standard) −182.2 ppm(m)

High polarity isomer: $^1$N-NMR(CDCl$_3$) δ3.66(s, 3H), 5.3(m, 1H), 5.54(m, 1H) $^{19}$F-NMR(CDCl$_3$, CCl$_3$F standard) −182.7 ppm(m)

Example 5-6

Preparation of 2,4-ethylene-3α-homo-7α-fluoro-17,20-dimethylPGI$_2$ methyl ester Using the low polarity isomer (115 mg, 0.17 mmol) among the compounds prepared in Example 5-5, the above identified compound (57 mg, yield: 75%) was prepared in the same manner as in Example 1-7. Using the high polarity isomer (102 mg, 0.15 mmol) among the compounds prepared in Example 5-5, the above identified compound (62 mg, yield: 91%) was prepared in the same manner as in Example 1-7.

Low polarity isomer: $^1$N-NMR(CDCl$_3$) δ0.8–2.8(m, 29H), 3.68(s, 3H), 3.90(m, 1H), 4.18(m, 1H0, 4.64(m, 2H), 5.37(m, 1H), 5.59(m, 2H) $^{19}$F-NMR(CDCl$_3$, CCl$_3$F standard) −184.5 ppm(m)

High polarity isomer: $^1$N-NMR(CDCl$_3$) δ0.8–2.8(m, 29H), 3.66(s, 3H), 3.90(m, 1H), 4.15(m, 1H), 4.4–4.7-(m, 2H), 5.38(m, 2H) $^{19}$F-NMR(CDCl$_3$, CCl$_3$F standard) −184.8 ppm(m)

REFERENCE EXAMPLE 25

Preparation of 3-(t-butyldimethylsiloxymethyl)cyclohexanecarboaldehyde

Using 1,3-cyclohexanedimethanol (48 g), the above identified compound (31 g) was prepared in the same manner as in Reference Example 18.

$^1$N-NMR(CDCl$_3$) δ0–0.1(m, 6H), 0.7–0.9(m, 9H), 1.0–2.4(m, 8H), 3.4–3.6(m, 2H), 9.6(s, 1H)

REFERENCE EXAMPLE 26

Preparation of 3-(2,2-dibromovinyl)cyclohexanemethanol t-butyldimethylsilyl ether Using the compound (14 g) prepared in Reference Example 25, the above identified compound (16 g) was prepared in the same manner as in Reference Example 19.

$^1$N-NMR(CDCl$_3$) δ0–0.1(m, 6H), 0.7–0.9(m, 9H), 1.2–1.8(m, 8H), 3.3–3.5(m, 2H), 6.2(m, 1H)

REFERENCE EXAMPLE 27

Preparation of 3-(3-tetrahydropyranyloxy-1-propynyl)cyclohexanemethanol t-butyldimethylsilyl ether Using the compound (16 g) prepared in Reference Example 26, the above identified compound (11.6 g) was prepared in the same manner as in Reference Example 20.

$^1$N-NMR(CDCl$_3$) δ0–0.1(m, 6H), 0.8–0.9(m, 9H), 1.2–2.3(m, 14H), 3.3–3.4(m, 2H), 3.4–3.6(m, 1H), 3.8–3.9(m, 1H), 4.1–4.3(m, 2H), 4.8–4.9(m, 1H)

REFERENCE EXAMPLE 28

Preparation of 3-(3-tetrahydropyranyloxy-1-propynyl)cyclohexanemethanol

Using the compound (11.6 g) prepared in Reference Example 27, the above identified compound (7.8 g) was prepared in the same manner as in Reference Example 21.

REFERENCE EXAMPLE 29

Preparation of 3-(3-tetrahydropyranyloxy-1-propynyl)cyclohexanecarboaldehyde

Using the compound (7.8 g) prepared in Reference Example 28, the above identified compound (6.0 g) was prepared in the same manner as in Reference Example 22.

$^1$N-NMR(CDCl$_3$) δ1.2–2.4(m, 14H), 3.4–3.6(m, 1H), 3.8–3.9(m, 1H), 4.2–4.4(m, 2H), 4.8–4.9(m, 1H), 9.6(m, 1H)

REFERENCE EXAMPLE 30

Preparation of 3-(3-hydroxy-1-propynyl)cyclohexanecarboxylic acid methyl ester

Using the compound (9 g) prepared in Reference Example 29, the above identified compound (3.8 g) was prepared in the same manner as in Reference Example 23.

$^1$N-NMR(CDCl$_3$) δ1.2–2.4(m, 8H), 3.7(s, 3H), 4.2–4.3(m, 2H)

REFERENCE EXAMPLE 31

Preparation of 3-(3-oxo-1-propynyl)cyclohexanecarboxylic acid methyl ester

Using the compound (3.8 g) prepared in Reference Example 30, the above identified compound (3.1 g) was prepared in the same manner as in Reference Example 24.

$^1$N-NMR(CDCl$_3$) δ1.2–2.6(m, 8H), 3.7(s, 3H), 9.2(m, 1H)

EXAMPLE 6

2,4-propylene-7α-fluoro-17,20-dimethylPGI$_2$ methyl ester

Example 6-1

Preparation of 2,4-propylene-5,6-dehydro-7-hydroxy-17,20-dimethylPGE$_2$ methyl ester 11,15-bis(t-butyldimethyl)silyl ether Using the aldehyde (0.92 g) prepared in Reference Example 31, the above identified compound (1.50 g) was prepared in the same manner as in Example 1-1.

Example 6-2

Preparation of 2,4-propylene-5,6-dehydro-7-trimethylsiloxy-17,20-dimethylPGF$_2α$ methyl ester (11,15-bis(t-butyldimethyl)silyl-9-triethylsilyl ether Using the compound (1.50 g) prepared in Example 6-1, the above identified compound (1.47 g) was prepared in the same manner as in Example 1-2.

$^1$N-NMR(CDCl$_3$) δ0.00–0.20(m, 21H), 0.50–0.70(m, 6H), 0.80–1.00(m, 33H), 3.58(s, 3H), 3.98–4.15(m, 2H), 5.32–5.60(m, 2H)

Example 6-3

Preparation of 2,4-propylene-5,6-dehydro-7β-fluoro-17,20-dimethylPGF$_2α$ methyl ester 11,15-bis(t-butyldimethyl)silyl-9-triethylsilyl ether Using the compound (1.47 g) prepared in Example 6-2, the above identified compound (0.90 g) was prepared in the same manner as in Example 1-3.

$^{19}$F-NMR(CDCl$_3$, CCl$_3$F standard) −169.5 ppm(m)

Example 6-4

Preparation of 2,4-propylene-5,6-dehydro-7β-fluoro-17,20-dimethylPGF$_2α$ methyl ester 11,15-bis(t-butyldimethyl)silyl ether Using the compound (0.90 g) prepared in Example 6-3, the above identified compound (488 mg) was prepared in the same manner as in Example 1-4.

$^1$N-NMR(CDCl$_3$) δ0.00–0.12(m, 12H), 0.80–1.00(m, 24H), 3.61(s, 3H), 4.00–4.18(m, 2H), 5.22–5.54(m, 2H)
$^{19}$F-NMR(CDCl$_3$, CCl$_3$F standard) −168.6 ppm(m)

Example 6-5

Preparation of 2,4-propyIyene-7α-fluoro-17,20-dimethylPGI$_2$ methyl ester 11,15-bis(t-butyldimethyl)silyl ether Using the compound (488 mg) prepared in Example 6-4, two types of isomers of the above identified compound i.e. a low polarity isomer (53 mg) and a high polarity isomer (48 mg) were prepared in the same manner as in Example 1-5, followed by Example 1-6.

Low polarity isomer: $^1$N-NNR(CDCl$_3$) δ0.00–0.20(m, 12H), 0.80–0.90(m, 24H), 2.59(s, 3H), 5.22(dd, J=57.9 Hz, 9 Hz, 1H), 5.42–5.48(m, 2H) $^{19}$F-NMR(CDCl$_3$, CCl$_3$F standard) −182.9 ppm(dd, J=60 Hz, 10 Hz)

High polarity isomer: $^1$N-NMR(CDCl$_3$) δ0.00–0.15(m, 12H), 0.78–0.90(m, 24H), 3.61(s, 3H), 5.22(dd, J=60 Hz, 9 Hz, 1H), 5.42–5.48(m, 2H) $^{19}$F-NMR(CDCl$_3$, CCl$_3$F standard) −182.4 ppm(dd, J=60 Hz, 10 Hz)

Example 6-6

Preparation of 2,4-propylyene-7α-fluoro-17,20-dimethylPGI$_2$ methyl ester

Using the low polarity isomer (53 mg) among the compounds prepared in Example 6-5, the above identified compound (27 mg) was prepared in the same manner as in Example 1-7. Using the high polarity isomer (48 mg) among the compound prepared in Example 6-5, the above identified compound (25 mg) was prepared in the same manner as in Example 1-7.

Low polarity isomer: $^1$N-NMR(CDCl$_3$) δ0.88–.0.96(m, 6H), 3.65(s, 3H), 3.82–4.00(m, 1H), 4.16–4.24(m, 1H), 4.46–4.52(m, 1H), 4.60–4.70(m, 1H), 5.38(dd, J=57 Hz, 9 Hz), 5.56–5.64(m, 2H) $^{19}$F-NMR(CDCl$_3$, CCl$_3$F standard) −184.8 ppm(dm, J=57 Hz) −186.8 ppm(dm, J=57 Hz)

High polarity isomer: $^1$N-NMR(CDCl$_3$) δ0.88–0.92(m, 6H), 3.65(s, 3H), 3.82–4.00(m, 1H), 4.16–4.24(m, 1H), 4.46–4.52(m, 1H), 4.60–4.70(m, 1H), 5.28(dd, J=58 Hz, 10 Hz, 1H), 5.58–5.61(m, 2H) $^{19}$F-NMR(CDCl$_3$, CCl$_3$F standard) −184.2 ppm(dm, J=58 Hz) −184.4 ppm(dm, J=58 Hz)

REFERENCE EXAMPLE 32

Preparation of 3(t-butyldimethylsiloxymethyl)cyclobutanecarbaldehyde

Using 1,3-cyclobutanedimethanol (4.11 g), the above identified compound (3.61 g) was prepared in the same manner as in Reference Example 18.

$^1$N-NMR(CDCl$_3$) δ0.07–0.13(m, 6H), 0.96(s, 9H), 1.98–2.60(m, 5H), 2.98–3.15(m, 1H), 3.51(d, J=5.4 Hz, 0.5H), 3.61(d, J=5.4 Hz, 0.5H), 9.67(d, J=3.2 Hz, 0.5H), 9.79(d, J=3.2 Hz, 0.5)

REFERENCE EXAMPLE 33

Preparation of 3-(2,2-dibromovinyl)cyclobutanemethanol t-butyldimethylsilyl ether Using the compound of (3.61 g) prepared in Reference Example 32, the above identified compound (5.35 g) was prepared in the same manner as in Reference Example 19.

$^1$N-NMR(CDCl$_3$) δ0.04(s, 3H), 0.06(s, 3H), 0.90(s, 9H), 1.80–2.50(m, 5H), 2.90–3.20(m, 1H), 3.50(d, J=5.1 Hz, 0.5H), 3.62(d, J=5.1 Hz, 0.5H), 6.44(d, J=8.4 Hz, 0.5H)

REFERENCE EXAMPLE 34

Preparation of 3-(3-tetrahydropyranyloxy-1-propynyl)cyclobutanemethhanol t-butyldimethylsilyl ether Using the compound of (5.35 g) prepared in Reference Example 33, the above identified compound (3.82 g) was prepared in the same manner as in Reference Example 20.

$^1$N-NMR(CDCl$_3$) δ0.04(s, 3H), 0.07(s, 3H), 0.90(s, 9H), 1.42–2.60(m, 11H), 2.80–3.10(m, 1H), m, 1H), 3.48–3.60(m, 3H), 3.78–3.94(m, 1H), 4.15–4.38(m, 2H), 4.78–3.84(m, 1H)

REFERENCE EXAMPLE 35

Preparation of 3-(3-tetrahydropyranyloxy-1-propynyl)cyclobutanemethanol

Using the compound of (3.82 g) prepared in Reference Example 34, the above identified compound (2.07 g) was prepared in the same manner as in Reference Example 21.

$^1$N-NMR(CDCl$_3$) δ1.40–2.65(m, 11H), 2.85(3.18(m, 1H), 3.50–3.70(m, 3H), 3.78–3.90(m, 1H), 4.15–4.38(m, 2H), 4.75–5.05(m, 1H)

REFERENCE EXAMPLE 36

Preparation of 3-(3-tetrahydropyranyloxy-1-propynyl)cyclobutanecarbaldehyde

Using the compound of (2.07 g) prepared in Reference Example 35, the above identified compound (1.96 g) was prepared in the same manner as in Reference Example 22.

$^1$N-NMR(CDCl$_3$) δ1.40–1.90(m, 6H), 2.18–2.55(m, 4H), 2.95–3.18(m, 2H), 3.46–3.60(m, 1H), 3.73–3.90(m, 1H), 4.12–4.36(m, 2H), 4.76(m, 1H), 9.65(d, 2.2 Hz, 0.6H), 9.77(d, 2.2 Hz, 0.5H)

REFERENCE EXAMPLE 37

Preparation of 3-(3-hydroxy-1-propynyl)cyclobutanecarboxylic acid methyl ester

Using the compound of (1.96 g) prepared in Reference Example 36, the above identified compound (1.24 g) was prepared in the same manner as in Reference Example 23.

$^1$N-NMR(CDCl$_3$) δ2.25–2.26(m, 4H), 2.90–3.10(m, 1H), 3.12–3.28(m, 1H), 3.68(s, 1.5H), 3.70(s, 1.5H), 2.47(m, 1H)

REFERENCE EXAMPLE 38

Preparation of 3-(3-oxo-1-propynyl)cyclobutanecarboxylic acid methyl ester

Using the compound of (1.24 g) prepared in Reference Example 37, the above identified compound (803 mg) was prepared in the same manner as in Reference Example 24.

$^1$N-NMR(CDCl$_3$) δ2.36–2.53(m, 2H), 2.60–2.75(m, 2H), 3.20–3.45(m, 2H), 3.70(s, 3H), 9.21(s, 1H)

EXAMPLE 7

2,4-methylene-7α-fluoro-17,20-dimethylPGI$_2$ methyl ester and sodium salt

Example 7-1

Preparation of 2,4-methylene-5,6-dehydro-7-hydroxy-17,20-dimethylPGE$_2$ methyl ester 11,15-bis(t-butyldimethyl)silyl ether Using the compound (803 mg) prepared in Reference Example 38, the above identified compound (1.60 g) was prepared in the same manner as in Example 1-1.

$^1$N-NMR(CDCl$_3$) δ0.01(m, 12H), 0.80–0.95(m, 24H), 3.66(m, 3H), 5.50–5.70(m, 2H)

Example 7-2

Preparation of
2,4-methylene-5,6-dehydro-7-trimethylsiloxy-17,20-dimethylPGE$_2\alpha$ methyl ester 11,15-bis(t-butyldimethyl)silyl-9-triethylsilyl ether Using the compound (1.60 g) prepared in Example 7-1, the above identified compound (1.54 g) was prepared in the same manner as in Example 1-2.

$^1$N-NMR(CDCl$_3$) δ0–0.2(m, 12H), 0.45–1.00(m, 48H), 3.73(m, 3H), 3.82–3.95(m, 1H), 4.10–4.25(m, 2H), 4.55–4.80(m, 2H), 5.40–5.70(m, 2H)

Example 7-3

Preparation of
2,4-methylene-5,6-dehydro-7β-fluoro-17,20-dimethylPGF$_2\alpha$ methyl ester 11,15-bis(t-butyldimethyl)silyl-9-triethylsilyl ether Using the compound (1.54 g) prepared in Example 7-2, the above identified compound (1.17 g) was prepared in the same manner as in Example 1-3.

$^1$N-NMR(CDCl$_3$) δ0–0.20(m, 12H), 0.50–1.0(m, 33H), 3.73(s, 1.5H), 3.75(s, 1.5H0, 3.85–3.95(m, 1H), 4.10–4.20(m, 1H), 4.21–4.35(m, 1H), 5.35(dm, J=46.6 Hz, 1H), 5.50(m, 2H) $^{19}$F-NMR(CDCl$_3$, CCl$_3$F standard) −170.1 ppm(m)

Example 7-4

Preparation of
2,4-methylene-5,6-dehydro-7β-fluoro-17,20-dimethylPGF$_2\alpha$ methyl ester 11,15-bis(t-butyldimethyl)silyl ether Using the compound (1.17 g) prepared in Example 7-3, the above identified compound (717 mg) was prepared in the same manner as in Example 1-4.

$^1$N-NMR(CDCl$_3$) δ0–0.15(m, 12H), 0.75–0.95(m, 24H), 3.71(s, 1.5H), 3.73(s, 1.5H), 4.08–4.20(m, 2H), 4.30–4.41(m, 1H), 5.40–5.50(m, 2H), 5.47,(dm, J=46.6 Hz, 1H) $^{19}$F-NMR(CDCl$_3$, CCl$_3$F standard) −168.2 ppm(m)

Example 7-5

Preparation of
2,4-methylene-7α-fluoro-17,20-dimethylPGI$_2$ methyl ester 11,15-bis(t-butyldimethyl)silyl ether Using the compound (710 mg) prepared in Example 7-4, the above identified compound (251 mg) was prepared in the same manner as in Example 1-5 followed by Example 1-6.

$^1$N-NMR(CDCl$_3$) δ0–0.10(m, 12H), 0.75–0.95(m, 24H), 3.66(s, 1.5H), 3.69(s, 1.5H), 3.75–3.90(m, 1H), 4.10–4.20(m, 1H), 4.48–4.80(m, 2H), 5.30(dm, J=56.5 Hz, 1H) $^{19}$F-NMR(CDCl$_3$, CCl$_3$F standard) −183.8(dd, J=56.5 Hz, 7.5 Hz), −184.2(dd, J=56.5 Hz, 7.5 Hz)

Example 7-6

Preparation of
2,4-methylene-7α-fluoro-17,20-dimethylPGI$_2$ methyl ester

Using the compound (251 mg) prepared in Example 7-5, the above identified compound (132 mg) was prepared in the same manner as in Example 1-7. The obtained compound (132 mg) was subjected to high performance liquid chromatography (silica, hexane:ethanol=96:4) to separate two types of isomers, whereby a low polarity isomer (55 mg) and a high polarity isomer (67 mg) were obtained.

Low polarity isomer: $^1$N-NMR(CDCl$_3$) δ0.80–0.90(m, 6H), 3.55–3.60(m, 1H), 3.60(s, 3H), 3.80–3.95(m, 1H), 4.05–4.15(m, 2H), 4.55–4.68(m, 2H), 5.41(dd, J= 60 Hz, 8.3 Hz, 1H), 5.50–5.71(m, 2H) $^{19}$F-NMR(CDCl$_3$, CCl$_3$F standard) −184.8 ppm(dd, J=60 Hz, 8.1 Hz)

High polarity isomer: $^1$N-NMR(CDCl$_3$) δ0.80–0.90(m, 6H), 3.50–3.60(m, 2H), 3.65(s, 3H), 3.80–3.98(m, 1H), 4.03–4.15(m, 2H), 4.58–4.66(m, 1H), 4.70–4.80(m, 1H), 5.44(dd, J=60 Hz, 8.3 Hz, 1H), 5.50–5.70(m, 2H) $^{19}$F-NMR(CDCl$_3$, CCl$_3$F standard) −184.8 ppm(dd, J=60 Hz, 8.3 Hz)

Example 7-7

Preparation of sodium salt of
2,4-methylene-7α-fluoro-17,20-dimethylPGI$_2$

The low polarity isomer (158 mg) among the compounds prepared in Example 7-6 was dissolved in ethanol (9.1 ml), and a 0.1N sodium hydroxide aqueous solution (3.94 ml) was added thereto under cooling with ice. The mixture was stirred at room temperature for 15 hours. The reaction solution was concentrated under reduced pressure, and the residue was dissolved in water (0.45 ml), and acetonitrile (13.8 ml) was added under stirring. the precipitated white solid was collected by filtration and dried to obtain the low polarity isomer (128 mg) of the above identified compound.

Using the high polarity isomer (188 mg) among the compounds prepared in Example 7-6, the high polarity isomer (156 mg) of the above identified compound was prepared in the same manner as above.

Low polarity isomer: $^1$N-NMR(CDCl$_3$) δ0.94–1.05(m, 6H), 1.18–1.85(m, 10H), 2.03–2.19(m, 2H0, 2,33–3.20(m, 7H), 3.86–4.00(m, 1H), 4.14–4.25(m, 1H), 4.60–4.76(m, 2H), 5.45(dd, J=60 Hz, 8.4 Hz, 1H), 5.55–5.78(m, 2H) $^{19}$F-NMR(CDCl$_3$, CCl$_3$F standard) −186.2 ppm(d, J=60 Hz)

High polarity isomer: $^1$N-NMR(CDCl$_3$) δ0.95–1.05(m, 6H), 1.18–1.82(m, 10H), 2.00–2.20(m, 2H), 2.50–2.78(m, 5H), 3.00–3.20(m, 1H), 4.15–4.25(m, 1H), 4.63–4.72(m, 1H), 4.86–4.94(m, 1H), 5.46(dd, J=60 Hz, 8.4 Hz, 1H), 5.57–5.80(m, 2H) $^{19}$F-NMR(CDCl$_3$, CCl$_3$F standard) −186.0 ppm(d, J=60 Hz)

REFERENCE EXAMPLE 39

Preparation of
3-(3-hydroxy-1-propynyl)cyclobutylacetic acid methyl ester

The compound (2.07 g) in Reference Example 35 was dissolved in methylene chloride (30 ml), and triethylamine (1.67 ml) and methane sulfonyl chloride (0.79 ml) were added thereto. The mixture was stirred at room temperature for one hour. To the reaction solution, a saturated sodium bicarbonate aqueous solution (20 ml) was added. Then, the organic layer was separated and dried over anhydrous magnesium sulfate. Then, the solvent was distilled off under reduced pressure. The residue thereby obtained was dissolved in N,N-dimethylformamide (50 ml) and water (10 ml), and potassium cyanide (0.78 g) was added thereto. The mixture was stirred at 80° C. for 7 hours. To the reaction solution, water (100 ml) was added, and the mixture was extracted with ethyl ether (20 ml×2). The organic layer was dried over anhydrous magnesium sulfate, and then the solvent was distilled off under reduced pressure.

The residue thereby obtained was dissolved in water (25 ml) and ethanol (25 ml), and potassium hydroxide (807 mg) was added thereto, and the mixture was stirred at 80° C. for 15 hours. Concentrated sulfuric acid was added thereto to adjust the pH 2, and sodium chloride was saturated. Then, the product was extracted with methylene chloride (30 ml×2). The extract was dried over anhydrous magnesium sulfate, and the solvent was distilled off under reduced pressure. The residue thereby obtained was dissolved in benzene (10 ml), and methanol (2 ml) and concentrated sulfuric acid (one drop) were added thereto. The solvent was distilled off under reduced pressure. The residue thereby obtained was purified by silica gel column chromatography to obtain the above identified compound (1.33 g).

$^1$N-NMR(CDCl$_3$) δ1.70–1.90(m, 1H), 1.95–2.10(m, 1H), 2.18–2.35(m, 1H), 2.35–2.60(m, 3H), 2.75–3.14(m, 2H), 3.65(s, 1.5H), 3.66(s, 1.5H), 4.23–4.30(m, 2H)

REFERENCE EXAMPLE 40

Preparation of 3-(3-oxo-1-propynyl)cyclobutylacetic acid methyl ester

Using the compound (1.33 g) prepared in Reference Example 39, the above identified compound (1.26 g) was prepared in the same manner as in Reference Example 24.

$^1$N-NMR(CDCl$_3$) δ1.88–2.00(m, 1H), 2.05–2.20(m, 1H), 2.35–2.75(m, 4.5H), 2.85–3.28(m, 1.5H), 3.66(s, 3H), 9.20(d, J=7.3 Hz, 1H)

EXAMPLE 8

1α-Homo-2,3-methylene-7α-fluoro-17,20-dimethylPGI$_2$ methyl ester

Example 8-1

Preparation of 1α-homo-2,3-methylene-5,6-dehydro-7-hydroxy-17,20-dimethylPGE$_2$ methyl ester 11,15-(t-butyldimethyl)silyl ether Using the compound (840 mg) prepared in Reference Example 40, the above identified compound (1.68 g) was prepared in the same manner as in Example 1-2.

$^1$N-NMR(CDCl$_3$) δ–0.1–0.15(m, 12H), 0.75–0.93(m, 24H), 3.65(3,3H), 4.10–4.20(m, 2H), 5.50–5.68(m, 2H)

Example 8-2

Preparation of 1α-homo-2,3-methylene-5,6-dehydro-7-trimethylsiloxy-17,20-dimethylPGF$_2$α methyl ester 11,15-bis(t-butyldimethyl)silyl-9-triethylsilyl ether Using the compound (1.68 g) prepared in Example 8-1, the above identified compound (1.58 g) was prepared in the same manner as in Example 1-2.

$^1$N-NMR(CDCl$_3$) δ–0.1–0.18(m, 12H), 0.50–0.68(m, 6), 0.72–1.00(m, 33H), 3.65(s, 3H), 3.82–4.98(m, 1H), 4.07–4.21(m, 2H), 4.55–4.76(m, 2H), 5.40–5.68(m, 2H)

Example 8-3

Preparation of 1α-homo-2,3-methylene-5,6-dehydro-7β-fluoro-17,20-dimethylPGF$_2$α methyl ester 11,15-bis(t-butyldimethyl)silyl-9-triethylsilyl ether Using the compound (1.58 g) prepared in Example 8-2, the above identified compound (1.22 g) was prepared in the same manner as in Example 1-3.

$^1$N-NMR(CDCl$_3$) δ0–0.1(m, 12H), 0.50–0.70(m, 6H), 0.75–0.98(m, 33H), 3.65(s, 3H), 4.03–4.18(m, 2H), 5.30–5.60(m, 3H) $^{19}$F-NMR(CDCl$_3$, CCl$_3$F standard) −168.4 ppm(m)

Example 8-4

Preparation of 1α-homo-2,3-methylene-5,6-dehydro-7β-fluoro-17,20-dimethylPGF$_2$α methyl ester 11,15-bis(t-butyldimethyl)silyl ether Using the compound (1.22 g) prepared in Example 8-3, the above identified compound (753 mg) was prepared in the same manner as in Example 1-4.

$^1$N-NMR(CDCl$_3$) δ0–0.1(m, 12H), 0.75–0.93(m, 24H), 3.65(s, 3H), 4.03–4.18(m, 2H), 5.30– 5.57(m, 3H) $^{19}$F-NMR(CDCl$_3$, CCl$_3$F standard) −168.1 ppm(m)

Example 8-5

Preparation of 1α-homo-2,3-methylene-7α-fluoro-17,20-dimethylPGI$_2$ methyl ester 11,15-bis(t-butyldimethyl)silyl ether Using the compound (753 mg) prepared in Example 8-4, the above identified compound (241 mg) was prepared in the same manner as in Example 1-5, followed by Example 1-6.

$^1$N-NMR(CDCl$_3$) δ0–0.15(m, 12H), 0.70–0.95(m, 24H), 3.62(s, 3H), 3.70–3.86(m, 1H), 4.12(m, 1H), 4.50–4.80(m, 2H), 5.27(dm, J=56.7 Hz), 5.48–5.54(m, 2H) $^{19}$F-NMR(CDCl$_3$, CCl$_3$F standard) −182.9 ppm(m)

Example 8-6

Preparation of 1α-homo-2,3-methylene-7α-fluoro-17,20-dimethylPGI$_2$ methyl ester Using the compound (241 mg) prepared in Example 8-5, the above identified compound (144 mg) was prepared in the same manner as in Example 1-7.

$^1$N-NMR(CDCl$_3$) δ0.85–1.00(m, 6H), 3.65(s, 1.5H), 3.66(s, 1.5H), 3.85–4.02(m, 1), 4.10–4.20(m, 2), 4.60–4.90(m, 2H), 5.26(dd, J=60 Hz, 8.4 Hz, 0.5H), 5.54–5.76(m, 2H) $^{19}$F-NMR(CDCl$_3$, CCl$_3$F standard) −183.7 ppm(dd, J=60 Hz, 8.1 Hz), −184.1 ppm(dd, J= 60 Hz, 8.1 Hz)

PREPARATIVE EXAMPLE 1 (GASTRIC CAPSULE)

50 mg of (1S*,3S*)-2,4-ethylene-7α-fluoro-17,20-dimethylPGI$_2$ methyl ester was dissolved in 10 ml of ethanol, and the solution was mixed with 18.5 g of mannitol. The mixture was passed through a 30 mesh sieve and dried at 30° C. for 90 minutes. It was again passed through a 30 mesh sieve.

To the powder thus obtained, 200 mg of Aerosil (microfine silica) was added, and the mixture was filled into 100 No. 3 hard gelatin capsules to obtain gastric capsules each containing 0.5 mg of (1S*,3S*)-2,4-ethylene-7α-flouro-17,20-dimethylPGI$_2$ methyl ester.

PREPARATIVE EXAMPLE 2 (INJECTABLE SOLUTION)

0.5 mg of 2,4-methylene-7α-fluoro-17,20-dimethylPGI$_2$ methyl ester was dissolved in 5 ml of ethanol, and the solution was sterilized by filtration through a bacteria retention filter and be placed in 0.1 ml portions in 1 ml ampoules to obtain ampoules each containing 10 μg of 2,4-methylene-7α-fluoro-17,20-dimethylPGI$_2$ methyl ester. Then, the ampoules were sealed. The content of each ampoule after dilution to an appropriate volume, for example, by diluting with Tris hydrochloric acid buffer solution of pH 8.6 to 1 ml, is suitable for use as an injectable solution.

PREPARATIVE EXAMPLE 3 (FREEZE-DRIED PREPARATION FOR INJECTABLE SOLUTION)

A solution comprising 50 mg of 2,4-methylene-7α-fluoro-17,20-dimethylPGI$_2$ sodium salt, 1.6 g of α-cyclodextrin and 10 ml of distilled water, 10 mg of citric acid, 50 g of lactose and 800 ml of distilled water were added and dissolved. The total volume was adjusted to 1 l with distilled water. Then, the solution was subjected to sterile filtration in a conventional manner and then be placed in 1 ml portions in ampoules, followed by freeze-drying and sealing to obtain a freeze-dried preparation for injectable solution.

We claim:

1. A novel prostaglandin I$_2$ derivative of the following formula (I)

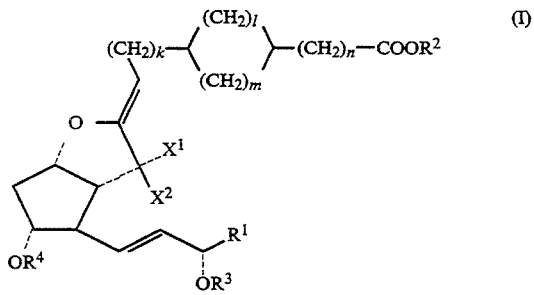

wherein $R^1$ is selected from the group consisting of $C_{1-10}$ alkyl, 1-methyl-3-pentenyl, 1-methyl-3-hexenyl, 1-methyl-3-pentynyl, 1-methyl-3-hexynyl, cyclopentyl, cyclohexyl, and cyclopentyl substituted with methyl, ethyl, propyl, butyl, pentyl, phenoxy, trifluoromethyl, or trifluoromethylphenoxy; $R^2$ is a hydrogen atom, a $C_{1-10}$ alkyl group or a cation; each of $R^3$ and $R^4$ which may be the same or different, is a hydrogen atom or a protecting group selected from the group consisting of tiralkylsilyl, triarylsilyl, triaralkylsilyl, alkanoyl, tetrahydropyranyl, tetrahydrofuranyl, benzoyl, and methoxyethoxy; one of $X^1$ and $X^2$ is a hydrogen atom and the other is a halogen atom selected from a fluorine atom and a chlorine atom, and k, l, m and n are integers of from 0 to 6, respectively, provided that $0 \leq k+n \leq 4$ and $1 \leq l+m \leq 6$.

2. The prostaglandin I$_2$ derivative according to claim 1, wherein the halogen atom is a fluorine atom.

3. The prostaglandin I$_2$ derivative according to claim 1, wherein $X^1$ is a fluorine atom, and $X^2$ is a hydrogen atom.

4. The prostaglandin I$_2$ derivative according to claim 1, wherein $X^1$ is a fluorine atom, $X^2$ is a hydrogen atom, $R^2$ is a group selected from a hydrogen atom, a $C_{1-4}$ alkyl group and an alkali metal ion, each of $R^3$ and $R^4$ is a hydrogen atom, and $R^1$ is a $C_{5-9}$ linear or branched alkyl group.

5. The prostaglandin I$_2$ derivative according to claim 4, wherein $R^1$ is an alkyl group selected from a n-pentyl group, a n-hexyl group, a 2-methylhexyl group and a 1,1-dimethylpentyl group.

6. The prostaglandin I$_2$ derivative according to claim 1, wherein k and n are integers of from 0 to 2, respectively, and l and m are integers of from 0 to 4, respectively, provided that $0 \leq k+n \leq 2$ and $1 \leq l+m \leq 4$, and yet each of $k+l+n$ and $k+m+n$ is not more than 4.

7. The prostaglandin I$_2$ derivatives according to claim 6, wherein $k+n=1$.

8. The prostaglandin I$_2$ derivative according to claim 6, wherein $k+n=0$.

9. The prostaglandin I$_2$ derivative according to claim 1, wherein the cycloalkylene group of the formula

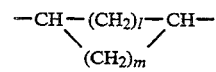

is a cycloalkylene group selected from a cyclopropylene group, a 1,2-cyclobutylene group, a 1,3-cyclobutylene group, a 1,2-cyclopentylene group, a 1,3-cyclopentylene group, a 1,2-cyclohexylene group, a 1,3-cyclohexylene group and a 1,4-cyclohexylene group.

10. The prostaglandin I$_2$ derivative according to claim 9, wherein $k+n=1$.

11. The prostaglandin I$_2$ derivative according to claim 9, wherein $k+n=0$.

12. A prostaglandin I$_2$ derivative selected from 2,3-methylene-7α-fluoro-17,20-dimethylPGI$_2$, 4-homo-2,3-methylene-7α-fluoro-17,20-dimethylPGI$_2$, 2,4-ethylene-7α-fluoro-17,20-dimethylPGI$_2$, 2,4-ethylene-3α-homo-7α-fluoro-17,20-dimethylPGI$_2$, 2,4-propylene-7α-fluoro-17,20-dimethylPGI$_2$, 2,4-methylene-7α-fluoro-17,20-dimethylPGI$_2$, 1α-homo-2,3-methylene-7α-fluoro-17,20-dimethylPGI$_2$, lower alkyl esters of these PGI$_2$ and sodium and potassium salts of these PGI$_2$.

13. A prostaglandin I$_2$ derivative selected from 2,4-methylene-7α-fluoro-17,20-dimethylPGI$_2$, its methyl ester and sodium salt.

* * * * *